(12) United States Patent
Wulfman et al.

(10) Patent No.: US 7,344,546 B2
(45) Date of Patent: *Mar. 18, 2008

(54) INTRALUMENAL MATERIAL REMOVAL USING A CUTTING DEVICE FOR DIFFERENTIAL CUTTING

(75) Inventors: Edward I. Wulfman, Woodinville, WA (US); Casey Torrance, Seattle, WA (US); Brent Nistal, Seattle, WA (US); Scott Youmans, Bothell, WA (US)

(73) Assignee: Pathway Medical Technologies, Redmond, WA (US)

( * ) Notice: Subject to any disclaimer, the term of this patent is extended or adjusted under 35 U.S.C. 154(b) by 517 days.

This patent is subject to a terminal disclaimer.

(21) Appl. No.: 10/442,888

(22) Filed: May 20, 2003

(65) Prior Publication Data

US 2004/0006358 A1    Jan. 8, 2004

Related U.S. Application Data

(63) Continuation-in-part of application No. 09/724,914, filed on Nov. 28, 2000, now Pat. No. 6,565,588.

(60) Provisional application No. 60/453,846, filed on Mar. 10, 2003, provisional application No. 60/194,805, filed on Apr. 5, 2000.

(51) Int. Cl.
*A61B 17/3207* (2006.01)
*A61B 17/22* (2006.01)

(52) U.S. Cl. .................... 606/159; 606/180
(58) Field of Classification Search ............. None
See application file for complete search history.

(56) References Cited

U.S. PATENT DOCUMENTS

| | | | |
|---|---|---|---|
| 3,854,916 A | | 12/1974 | Dochterman |
| 4,445,509 A | * | 5/1984 | Auth .................... 606/159 |
| 4,679,557 A | | 7/1987 | Opie et al. |
| 4,700,705 A | | 10/1987 | Kensey et al. |
| 4,790,813 A | * | 12/1988 | Kensey .................. 604/22 |
| 5,026,384 A | | 6/1991 | Farr et al. |
| 5,122,134 A | * | 6/1992 | Borzone et al. .......... 606/80 |
| 5,171,244 A | * | 12/1992 | Caspari et al. .......... 606/88 |
| 5,211,651 A | * | 5/1993 | Reger et al. ........... 606/159 |

(Continued)

FOREIGN PATENT DOCUMENTS

EP          0 551 706 B1      9/1992

(Continued)

*Primary Examiner*—Glenn K. Dawson
(74) *Attorney, Agent, or Firm*—Janet Sleath; Ann W. Speckman; Speckman Law Group PLLC

(57) ABSTRACT

Intralumenal material removal systems are provided using an advanceable and rotatable cutter assembly designed for differential cutting. The intralumenal material removal system includes a cutter assembly positionable in the body cavity of a mammalian subject. One embodiment of the cutter assembly includes a cutter with blades that are designed and arranged to form an acute blade angle of attack with the matter-to-be-removed. The cutter assembly is axially advanceable by translating the drive shaft and rotatable by rotating the drive shaft. The occlusive material is scraped by the cutter assembly and may be aspirated to remove the material from the body cavity. The cutter assembly may provide aspiration ports positioned between facing surfaces of the blades.

12 Claims, 18 Drawing Sheets

U.S. PATENT DOCUMENTS

| | | | |
|---|---|---|---|
| 5,228,459 A * | 7/1993 | Caspari et al. | 128/898 |
| 5,234,451 A | 8/1993 | Osypka | |
| 5,282,813 A | 2/1994 | Redha | |
| 5,304,181 A * | 4/1994 | Caspari et al. | 606/80 |
| 5,404,699 A * | 4/1995 | Christensen et al. | 56/104 |
| 5,609,602 A | 3/1997 | Machemer et al. | |
| 5,681,336 A * | 10/1997 | Clement et al. | 606/159 |
| 5,694,951 A * | 12/1997 | Bonutti | 128/898 |
| 5,759,185 A * | 6/1998 | Grinberg | 606/80 |
| 5,913,867 A * | 6/1999 | Dion | 606/180 |
| 6,126,667 A | 10/2000 | Barry | |
| 6,332,886 B1 * | 12/2001 | Green et al. | 606/80 |
| 6,482,217 B1 | 11/2002 | Pintor et al. | |
| 6,503,261 B1 * | 1/2003 | Bruneau et al. | 606/159 |
| 6,565,588 B1 * | 5/2003 | Clement et al. | 606/180 |
| 6,818,001 B2 * | 11/2004 | Wulfman et al. | 606/159 |

FOREIGN PATENT DOCUMENTS

| | | |
|---|---|---|
| WO | WO 00/51504 | 8/2000 |

* cited by examiner

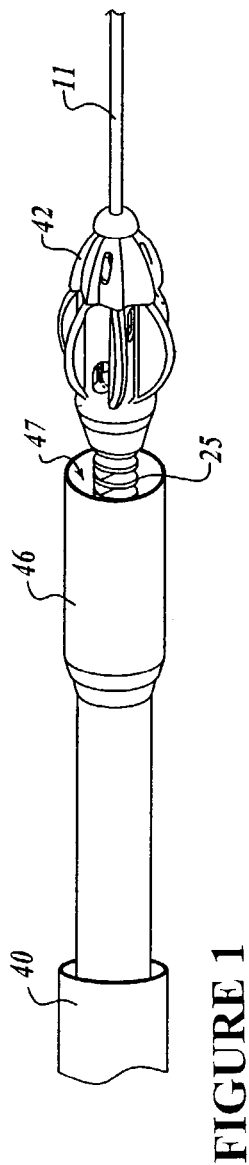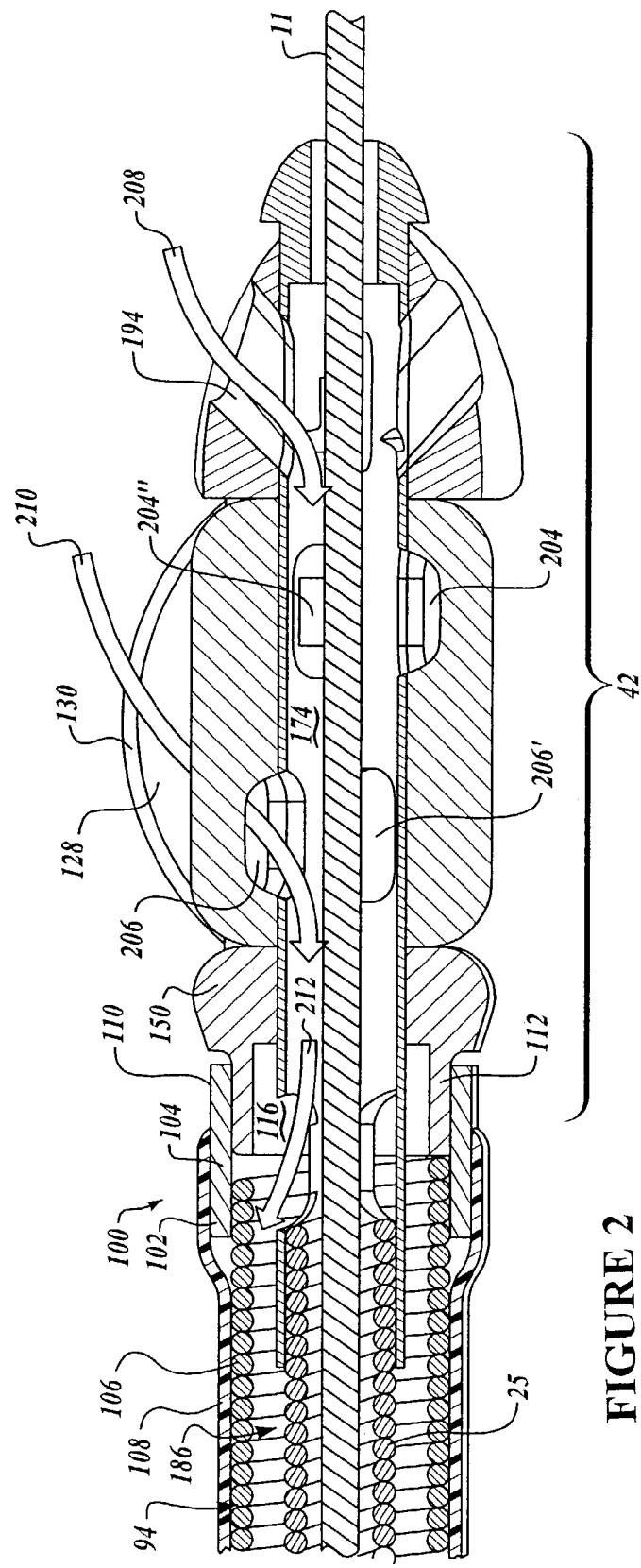
FIGURE 1
FIGURE 2

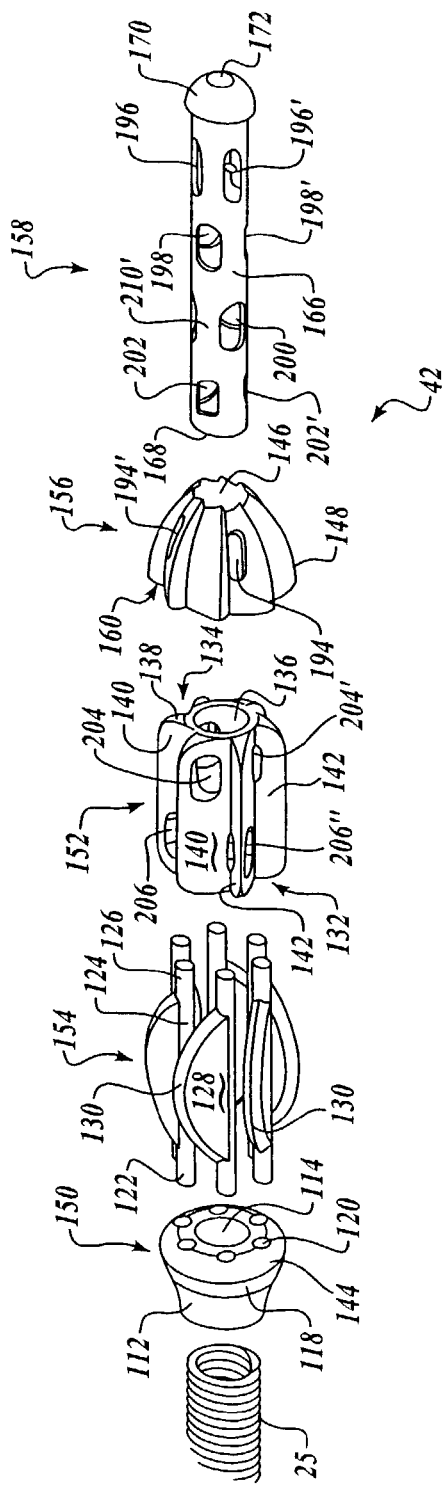
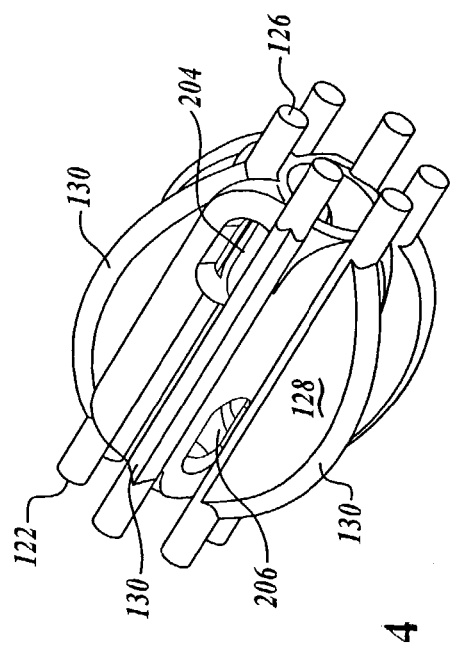
FIGURE 3
FIGURE 4

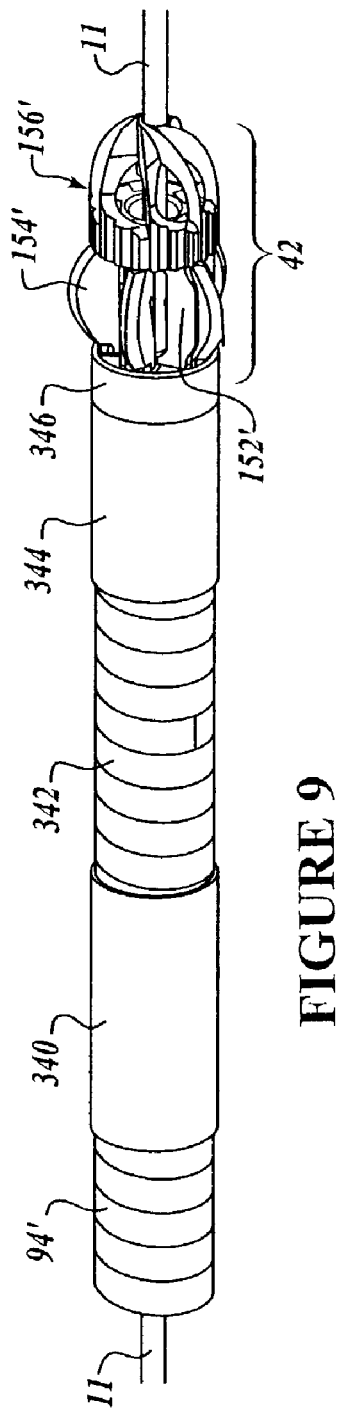
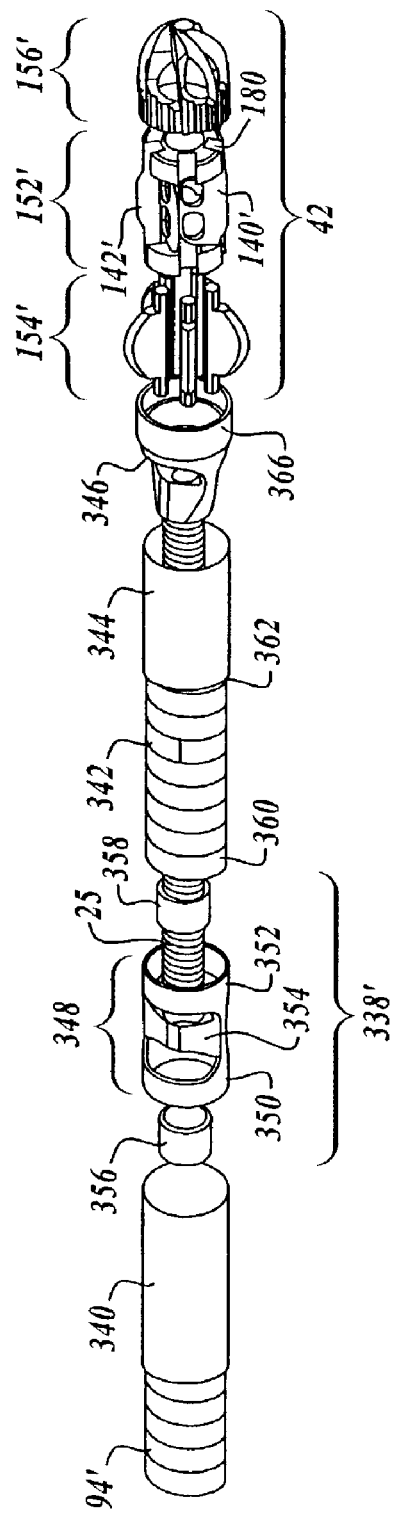
FIGURE 9
FIGURE 10

INTRALUMENAL MATERIAL REMOVAL USING A CUTTING DEVICE FOR DIFFERENTIAL CUTTING

CROSS-REFERENCE TO RELATED APPLICATIONS

This application is a continuation-in-part of U.S. patent application Ser. No. 09/724,914 filed on Nov. 28, 2000 and issued as U.S. Pat. No. 6,565,588 on May 20, 2003, which claims priority under 35 U.S.C. §119(e) to U.S. Provisional Patent Application No. 60/194,805, filed Apr. 5, 2000. The disclosures of the aforementioned applications are herein incorporated by reference in their entirety. This application also claims priority under 35 U.S.C. §119(e) to U.S. Provisional Patent Application No. 60/453,846 filed Mar. 10, 2003.

FIELD OF THE INVENTION

The present invention relates to systems and methods for removing material, such as obstructions and partial obstructions, from a body cavity of a mammalian subject, such as a blood vessel. More particularly, the present invention relates to systems and methods for removing material from a cavity of a mammalian subject using a rotatable cutter assembly having blades designed for differential cutting.

BACKGROUND OF THE INVENTION

In the medical field it is often required that a medical practitioner manipulate devices within a body cavity residing in a patient. In some cases, undesirable matter may exist or become lodged within the cavity and must be removed by the practitioner. At times, accumulation of the matter may reduce or cut off the flow of fluid, such as blood, and other essential components through the body cavity.

Some procedures for removing undesirable matter involve the challenging operation of maneuvering a cutting device within small confines of interior body cavities. In order to lead the cutting device to the site for removal of the matter, it must be routed through various internal structures, and the path through the body to the removal site may be tortuous. Usually, the cutting device is coupled to or otherwise associated with various devices, such as a drive shaft, guide wire, catheter(s), etc. that may guide the cutting device to the removal site.

One application for a cutting device is to remove atherosclerotic obstructions and partial obstructions. The use of rotating cutter assemblies is an established therapeutic intervention, and many different atherectomy methods and devices have been conceived and developed. Many of these systems involve placement of a guide catheter, a guidewire and a cutting device in proximity to an obstruction or partial obstruction in a blood vessel and then advancing and rotating the cutting device to cut or ablate the obstruction.

The following U.S. patents describe many types and specific features of devices for removing matter, which may be useful in atherectomy procedures: U.S. Pat. Nos. 4,898, 575; 5,127,902; 5,409,454; 5,976,165; 5,938,670; 5,843, 103; 5,792,157; 5,667,490; 5,419,774; 5,417,713; 4,646, 736; 4,990,134; 4,445,509; 5,681,336; 5,695,507; 5,827, 229; 5,938,645; 5,957,941; 5,019,088; 4,887,613; 4,895, 166; 5,314,407; 5,584,843; 4,966,604; 5,026,384; 5,019, 089; 5,062,648; 5,101,682; 5,112,345; 5,192,291; 5,224, 945; 4,732,154; 4,819,634; 4,883,458; 4,886,490; 4,894, 051; 4,979,939; 5,002,553; 5,007,896; 5,024,651; 5,041, 082; 5,135,531; 5,192,268; 5,306,244; 5,443,443; and 5,334,211. These U.S. patents are incorporated by reference herein in their entireties.

Despite the varied approaches to the systems and methods exemplified by the U.S. patents cited above, many challenges remain in providing systems and methods for removing material from a lumen, such as a blood vessel, safely and reliably and without causing complications. The safety and reliability of the system is manifestly critical.

The cutting device must not damage delicate beneficial material, such as the walls of a structure or other healthy tissue, which often surrounds the unwanted matter. Thus, it is important for a cutting device to separate the unwanted matter from the beneficial material in a safe manner that is not so aggressive as to damage the beneficial material. Much attention is required in designing such a cutting device that has an optimal cutting surface and material removal mechanism.

Some special devices are designed to ablate unwanted matter without harming beneficial material by a method known as differential cutting. Differential cutting is based on the observation that oftentimes the unwanted matter located in the cavity is rigid and has a less elastic quality than the beneficial material of the body cavity. Generally, the beneficial material, such as the wall of a blood vessel wall, has a shear modulus of elastic stiffness that is a relatively low value. As a result, when a blade that is designed for differential cutting contacts the beneficial material, the material becomes deformed at the point of contact and large shear stresses in the beneficial material are not exerted. By comparison, the unwanted matter is generally more rigid and has a higher value of shear modulus of elastic stiffness. Harder material is not able to deform when contacted by the differential cutting blade, and shear stresses are consequently exerted on the more rigid material. In this manner, fragments of the harder, undesirable matter are cut away by differential cutting blades, while the more elastic, beneficial material is unharmed.

Various cutting devices have been proposed that utilize differential cutting principles. U.S. Pat. No. 4,445,509 describes differential cutting in the context of an atherectomy device. Some differential cutting devices have particular features to allow for differential cutting, such as the use of diamond grit on a cutting surface. This diamond grit surface forms random angles of attack and creates random cutting characteristics at various points of contact with the target undesired matter. In using diamond grit cutting devices, when applying increased depth of force of the device into the target matter to be removed, there is a greater risk of cutting into the supporting beneficial material in proximity to the target undesired matter. Thus, these prior devices require extreme caution in use in order to avoid cutting beneficial material.

One of the particular challenges of removing matter from the interior of lumens is that the drive and cutter assemblies must be small enough and flexible enough to travel over a guidewire to a desired material removal site, such as the site of an obstruction or occlusion. Yet, the drive and cutter assemblies must be large enough and have structural integrity sufficient to operate reliably and effectively to cut or scrape the obstruction. Additionally, removal of the debris from the material removal site using an aspiration system is generally desirable. The drive and cutter assemblies therefore desirably incorporate a debris removal system as well.

The size and consistency of the material comprising an obstruction are frequently not well characterized prior to introduction of the material removal device. Thus, although devices and cutters having different sizes and properties may be provided, and may even be interchangeable on a material removal system, it is difficult to ascertain which combination of features is desired in any particular operation prior to insertion of the device. The use of multiple cutter assemblies having different properties during a materials removal operation is inconvenient at best, since it requires removal of each independent device and interchange of the cutter assemblies, followed by reinsertion of the new cutter assembly, or of a new device entirely. Interchange and reinsertion of cutter assemblies is time consuming and generally deleterious to the health and condition of the patient undergoing the procedure.

Many different types of expandable cutters have been conceived in an effort to provide a cutter having a small diameter profile that may be conveniently delivered to and removed from the site of the desired material removal, and that is expandable at the site to provide a larger diameter cutter. The following U.S. patents disclose various approaches to expandable cutter assemblies: U.S. Pat. Nos. 5,540,707; 5,192,291; 5,224,945; 5,766,192; 5,158,564; 4,895,560; 5,308,354; 5,030,201; 5,217,474; 5,100,425; and 4,966,604. These U.S. patents are incorporated by reference herein in their entireties.

Although numerous approaches to cutter assemblies have been developed, there is still a need for a cutter assembly that is conveniently navigable to the material removal site and that that removes matter of different types in a safe and effective manner, without harming surrounding beneficial material.

SUMMARY OF INVENTION

Methods and intralumenal material removal systems of the present invention involve a material removal component, referred to herein as a "cutter" or "cutter assembly". The cutter assembly is positionable in a lumen of a mammalian subject and operably connected to system controls, mechanical and power systems, usually by means of a rotating drive shaft. The cutter assembly comprises one or more distally located cutting or abrading head(s) having one or more cutting and/or abrading surfaces and is advanceable by translating the drive shaft and rotatable by rotating the drive shaft.

According to one embodiment of the present invention, the removal system comprises a cutter assembly having blades that are specially designed and arranged to cut or scrape matter while not damaging other beneficial material, or at least doing minimal damage to such beneficial material. The blades are provided at acute angles of attack, generally less than 90 degrees.

The cutter assembly may be either fixed or adjustable in diameter. In one particular embodiment, an expandable cutter is adjustable between a smaller diameter condition, in which it may be guided to and withdrawn from the desired material removal site, and a larger diameter condition, in which it may be operated during a material removal operation. The expandable cutter may thus be introduced to and withdrawn from the material removal site in a retracted, smaller diameter condition that facilitates translation and navigation of the device through various lumens, such as blood vessels. The expandable cutter may be selectively expanded at the material removal site to facilitate cutting, removal and aspiration of the material desired to be removed.

The material removal system often provides removal of debris, generally via aspiration through one or more material removal ports in the cutter assembly or another component in proximity to the cutter assembly. Debris generated during a material removal operation is removed by aspiration through the material removal ports and withdrawn through a sealed lumen formed, for example, between the cutter assembly drive shaft and a catheter. The sealed lumen is connectable to a vacuum source and aspirate collection system. The ports may be disposed between facing surfaces of the blades.

According to one embodiment, the material removal device of the present invention comprises multiple cutting members that may have different characteristics. For example, dual cutting and/or abrading members may be provided, one of which is expandable and one of which has a fixed diameter. In one embodiment, a fixed diameter cutter is mounted distal to an expandable diameter cutter. The fixed diameter cutter may take any of a variety of configurations and, according to one embodiment, has a generally ovoid profile and a plurality of cutting flutes. The fixed diameter cutter may also be provided with ports and/or cutouts that may be selectively employed as aspiration or infusion ports. The expandable diameter cutter, positioned proximal to the fixed diameter cutter, may also be provided with ports that may be selectively employed as aspiration or infusion ports. Any one or all of the cutters may be designed for differential cutting, according to the designs presented herein.

In one embodiment, the cutter assembly drive shaft operates bidirectionally and the adjustable diameter cutter is expanded or retracted selectively and controllably upon rotation in opposite directions. Upon rotation of the drive shaft and dual cutter assembly in a first direction, the fixed diameter cutter is used as the primary cutter and the expandable cutter remains in a smaller diameter condition, while upon rotation of the dual cutter assembly in a second direction, opposite the first, the expandable cutter is in a larger diameter condition and serves as the primary cutter. The present invention uses hydrodynamic, centrifugal and/or frictional forces to expand and contract the dual cutter assembly, thereby obviating the need for additional actuation systems, which add considerable complexity and rigidity to such systems.

Liquid infusion may be provided in proximity to the cutter assembly in addition to or alternatively to aspiration. Infusion of liquids may be used to provide additional liquids for materials removal or to deliver lubricating fluids, treatment agents, contrast agents, and the like. Infusion of fluids in proximity to the area of a material removal operation may be desirable because it tends to reduce the viscosity of the materials being removed, thus facilitating removal through relatively small diameter lumens. Infusion of liquids also desirably tends to reduce the volume of blood removed during the operation. According to one embodiment, a sealed lumen formed between the cutter assembly drive shaft and a catheter may alternatively and selectively be used as aspirate removal system and an infusion system. The sealed lumen may thus be selectively connectable to a vacuum source and aspirate collection system for aspiration, and an infusion source for infusion of liquids. Ports in or in proximity to the cutter assembly may be thus be employed, selectively, as aspiration and infusion ports.

According to another embodiment, an infusion system may be provided in addition to and independent of the aspiration system. In one embodiment, an infusion sleeve is provided that extends distal to the material removal element. The infusion sleeve is sealed for the length of the catheter and incorporates distal infusion ports. The infusion sleeve may extend through the lumen formed by the drive shaft and may be fixed, or usually, translatable with respect to the cutter assembly.

BRIEF DESCRIPTION OF THE DRAWINGS

FIG. 1 shows one embodiment of the present invention highlighting the distal end of a primary sheath with an expandable cutter assembly in the expanded condition;

FIG. 2 shows an enlarged, partially cross-sectional perspective view of one embodiment of an expandable cutter assembly and associated connections with the drive shaft and flexible conduit catheter;

FIG. 3 shows an enlarged, exploded perspective view of one embodiment of an expandable cutter assembly of the present invention;

FIG. 4 shows an enlarged, side perspective view of one embodiment of the cutting members in association with the central block of an expandable cutter assembly of the present invention;

FIGS. 7A-7C illustrate blade angles, wherein FIG. 7A shows a side view of one cutter assembly, FIG. 7B is a cross-sectional view depicting the blade angle of the blades in the cutter assembly of FIG. 7A, according to one embodiment of the present invention, and FIG. 7C illustrates a prior art cutting device;

FIGS. 8A and 8B are schematic diagrams illustrating blade angles, wherein FIG. 8A illustrates a blade angle of attack according to one embodiment of the present invention, and FIG. 8B illustrates one prior art cutting device;

FIG. 9 shows another embodiment of the present invention illustrating the distal end of a coiled metallic catheter with a cutter assembly in the expanded configuration;

FIG. 10 depicts the embodiment of FIG. 9 in a exploded perspective;

FIGS. 15A-15B are schematic diagrams illustrating exemplary curved blades of a cutter assembly, wherein FIG. 15A shows a cup-shaped cutter assembly with symmetrically curved and gradually sloping blades, and FIG. 15B shows a single blade having an asymmetrically curved profile;

FIGS. 16A-16D are schematic cross-sectional diagrams illustrating different numbers of blades according to various embodiments of the present invention, wherein FIG. 16A shows seven blades, FIG. 16B shows six blades, FIG. 16C shows five blades, and FIG. 16D shows three blades;

FIGS. 17A and 17B are schematic diagrams illustrating ports, wherein FIG. 17A shows an internal cut-away view of a cutter assembly with ports, according to one embodiment of the present invention, and FIG. 17B shows a cutter assembly with an exploded view of a port;

FIG. 18A is a prospective view from the distal to proximal ends of the cutter assembly, FIG. 18B is a prospective view from the proximal to distal ends of the cutter assembly, and FIG. 18C is an angled side view of the cutter assembly.

DETAILED DESCRIPTION OF PREFERRED EMBODIMENTS

Figure 5A:
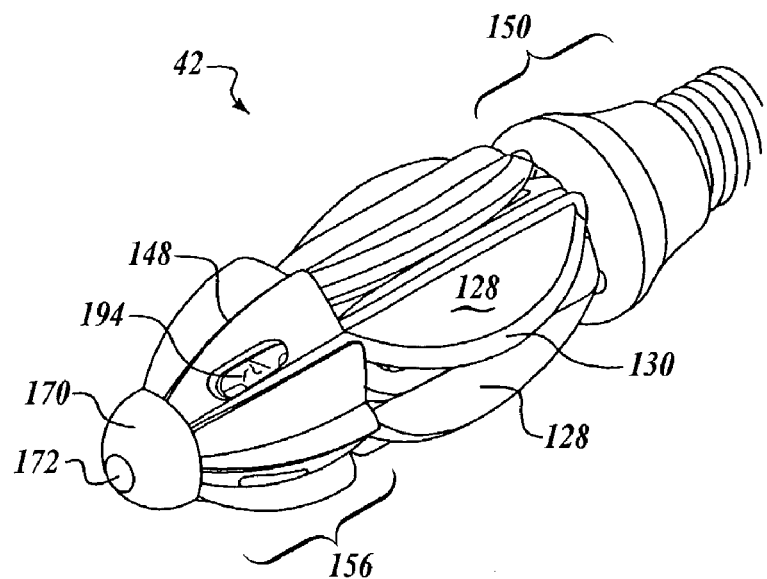
FIG. 5A illustrates an enlarged, perspective view of one embodiment of a dual cutter assembly of the present invention with the cutter assembly in a contracted configuration.
Figure 5B:
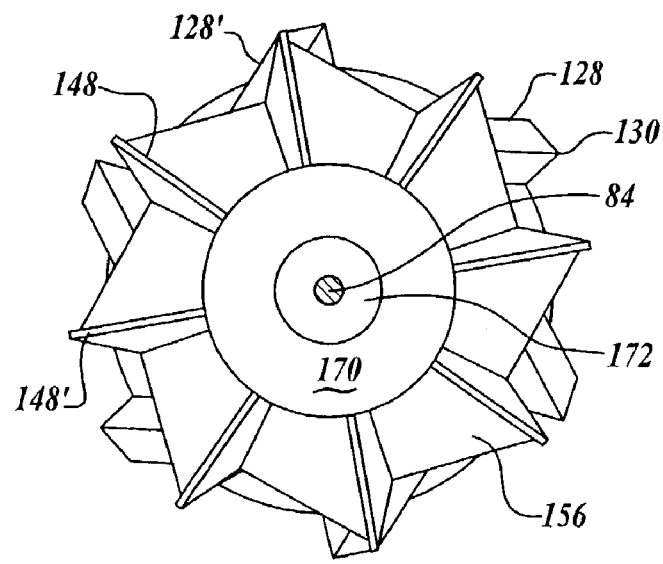
FIG. 5B illustrates an enlarged, front view of one embodiment of the dual cutter assembly of FIG. 5A with the cutter assembly in a contracted configuration.

As used herein in the description of various components, "proximal" or "antegrade" refers to a direction toward the system controls and the operator along the path of a drive system, and "distal" or "retrograde" refers to the direction away from the system controls and the operator and toward or beyond a terminal end of the cutter assembly. In general, the material removal system of the present invention comprises a cutter assembly positioned at the distal end of the material removal system.

Exemplary material removal systems, components and subassemblies suitable for use in connection with methods and systems of the present invention are disclosed and described in the U.S. patents incorporated herein by reference, and in PCT Patent Publication WO 01/76680, entitled "Intralumenal Material Removal Systems and Methods", which is incorporated herein by reference in its entirety. In particular embodiments, cutter blades of the cutter assembly operate according to differential cutting principles.

The cutter assembly is guided to the material removal site and is actuated to cut, grind or ablate, or otherwise separate the occlusive material from the beneficial material in proximity to the occlusive material, and to remove the occlusive material from the site. The removal system incorporating the cutter assembly may also include numerous other components that facilitate operation of the cutter assembly, according to the present invention. For example, the removal system may include a control unit, catheter assembly and/or manifold assembly, all of which remain outside the body during a material removal operation. In one embodiment, an advancer system may be integrated in the control unit and may incorporate one or more slip seals for the cutter assembly drive shaft, aspiration and/or infusion connections, and additionally may incorporate a track system for axially displacing the rotating cutter assembly drive shaft and cutter assembly relative to the control unit. The control unit may comprise a base arranged so that the control unit may be stably supported on a work surface or a body surface during material removal operations. The control unit also may incorporate control systems for actuating, adjusting and providing system information concerning power, drive shaft rpm, cutter assembly drive shaft axial translation, aspiration, infusion and the like.

In other embodiments of a material removal system of the present invention, the control unit may remotely control operation of the cutter assembly, the control unit communicating instructions by sending signals to the various other components of the removal system, e.g. using stereotactic techniques. The cutter assembly may further be guided to the removal site through a variety of local or remote mechanisms, such as magnetic forces, electrical means, etc.

In some embodiments of the material removal system, the cutter assembly may be guided to the removal site using a guidewire. In these cases, the cutter assembly may be translated over the guidewire. The guidewire is navigated through one or more lumens in a subject, such as blood vessels, to a desired material removal site. Many suitable guidewires are known in the art, including flexible guidewires, and may be used with the material removal system of the present invention. Guidewires having a diameter of from about 0.009 inch to about 0.018 inch and having an atraumatic tip are often used.

A guiding catheter may be used for guiding the guidewire, and subsequently the cutter assembly, to the lumen or other body cavity to be treated, as is typical and well known in the art for interventions in coronary, vein graft or peripheral arteries. In operation, the guiding catheter and the guidewire are generally introduced into a lumen of a patient, such as the femoral artery, and navigated or guided to the site of the desired material removal operation.

A guidewire brake or clamp is often provided in proximity to or integrated with the material removal system to hold the guidewire in a stationary, fixed position during operation of the cutter assembly. Rotation and axial displacement of the guidewire may be prevented using either an automatic or a manual grip. An automatic guidewire braking system may be implemented using a solenoid-activated brake that is automatically actuated to brake during activation of the cutter assembly motor drive. A manual guidewire braking system may be actuated by a manual, over-center clamp, cam and brake shoe assembly or another mechanical device. An interlock system may be incorporated in connection with a manual brake system to prevent actuation of the cutter assembly drive system if the guidewire is not in a clamped, stationary condition.

An aspiration source, such as a roller pump, may be provided to provide aspiration to the cutter assembly. There may also be a collection vessel such as a collection bag or, for example, a commercially available evacuated container having a suitable volume. Alternatively, the aspiration source may be provided as a syringe or similar device actuated by a motor, pressurized gas, or the like. The aspiration source may alternatively be provided as a small, electrical vacuum pump with a suitable collection device.

The configuration and construction of the control unit and the manifold assembly may vary, depending on specific desired applications for intralumenal material removal. Some suitable designs and configurations are well known in the art. In some embodiments, a control unit is provided as a separate unit in electrical and operating communication via a flexible cable with an advancer unit. An advancer unit may be configured ergonomically and constructed for placement in proximity to and/or in contact with the patient. In one embodiment, the base of advancer unit is configured to rest stably on the leg of a patient while a material removal operation takes place. A tracking unit may additionally have a work platform providing a level surface for use of the operator and associated medical professionals.

In one embodiment, a control unit houses various components, such as a programmable logic controller and power source in operable communication to provide power and to control operation of a vacuum control unit, a cutter assembly advancer unit, a guidewire brake unit, a cutter assembly drive system, an aspiration control unit and/or a temperature control unit. The control unit may be provided as a separate console and may incorporate various displays for providing information concerning operating conditions and feedback from the material removal site to the operator. According to one embodiment, the control unit provides continuously updated output to an operator including such operating parameters such as temperature at the material removal site; cutter assembly rotation rate and/or advance rate; aspiration rate and/or volume; infusion rate and/or volume; and the like. The control unit may additionally provide adjustable controls permitting the operator to control operating parameters of the cutter assembly and material removal operation. Alternatively, adjustable controls and feedback data may be incorporated in an advancer unit, or a single integrated control and advancer unit may be provided.

The vacuum control unit may comprise, for example, a solenoid operated vacuum valve. The cutter assembly advance system may comprise, for example, a stepper motor. A guidewire brake unit may comprise, for example, a solenoid actuated braking device. The cutter assembly drive system for rotating the cutter assembly may be operated using a pneumatic- or electric-powered motor. The aspiration control may comprise, for example, a vacuum assist motor/pump. The temperature control monitor may be in operable communication with a temperature probe providing continuous or intermittent feedback relating to the temperature or temperature changes at the site of the material removal operation.

In some embodiments of the present invention, a high-speed electric motor supplied by a power source, e.g. a battery, is utilized for the cutter assembly drive system. The motor may be geared and/or separated by a short flexible drive shaft that couples the motor to the cutter assembly drive shaft. The motor may thus be mounted off-axis with respect to the cutter assembly drive shaft. This arrangement also permits translation and advancing of the cutter assembly drive shaft independent of the motor, permitting the motor to remain stationary during material removal operations. In alternative embodiments, the motor assembly and other components, such as the drive shaft and cutter assembly may be axially translatable in the advancer unit, as described in more detail below.

According to some embodiments of the material removal system of the present invention, the drive system may be unidirectional and capable of rotating the cutter assembly drive shaft in one rotational direction, or it may be selectively bidirectional and capable of rotating the drive shaft selectively in both a clockwise and counterclockwise direction. The drive system is also usually capable of rotating drive shaft at variable speeds ranging from 500 rpm to 150,000 rpm, more often from 500 to 60,000 rpm. In an exemplary embodiment of the invention, drive system is a direct current variable speed micro-motor capable of operating at rotational speeds of from 500 rpm to 150,000 rpm. It is understood that a variety of motors may be employed in the system and the range of speeds and capabilities may vary according to the type and site of material removed, and the type of cutter assembly utilized. The present invention also contemplates the use of alternative means of rotating the drive shaft, such as air-driven turbines, and the like.

A proximal end of the drive shaft is operably connected directly, or via a coupler or transmission system, to the drive system, while a distal end of the drive shaft is operably connected, directly or via a coupler, to the cutter assembly mounted to a distal end of the drive shaft. In one embodiment, the drive shaft is a flexible, hollow, helical, torque-transmitting shaft. Hollow, multi-filar metallic drive shafts are known in the art and are suitable for use with the material removal system and cutter assembly of the present invention. The cutter assembly drive shaft may be a multi-filar stainless steel coil drive shafts having a bi- tri- or quad-filar construction. Coil drive shafts having an inner diameter of from about 0.015 to 0.025 inch and an outer diameter of from about 0.025 to 0.035 inch are generally suitable for atherectomy applications.

One embodiment of system has a tracking unit for axially translating drive shaft and associated components. The tracking unit may comprise a body having one or more axial translation mechanisms, such as rails running along the longitudinal axis of a bed on which rides a motor assembly. Alternative embodiments of the present invention may employ any conventional axial translation mechanisms including rails, slots, tracks, wheels, and the like. The motor assembly may engage rails to permit controllable axial translation in either an antegrade or retrograde direction, which in turn facilitates axial translation of expandable cutter assembly and associated components. The motor assembly may house several components and assemblies, such as, but not limited to one or motors, drive shafts, gear drives and the like. A guide wire brake system may be fixedly connected to the proximal end of the tracking unit and serve to releasably restrict axial and rotational movement of the guide wire. In this particular embodiment, a movement-restricting mechanism, such as a cam-lever and brake shoe(s) assembly, may comprise the guidewire brake system. Embodiments of the present invention may incorporate any conventional movement-restriction mechanism or mechanisms which serve to controllably limit axial and rotational movement of the guide wire. The tracking unit may further comprise a cover encompassing the motor assembly and the bed. In addition, a locking mechanism may be provided to the tracking unit that controllably restricts axial movement of motor assembly. Any conventional locking mechanism may be employed in the present invention, such as, but not limited to a system whereby a restrictive force is exerted from tracking unit cover to the motor assembly. For example, an element may extend from the top face of motor assembly through a longitudinal slot in the tracking unit cover which may be held in tight association with the cover by a clamping device, such as a threaded knob. Of course, various embodiments of the present invention envision may include any of a wide variety of conventional locking mechanisms.

The guide wire usually passes through the cutter assembly, catheter, motor system and wire brake and exits out the proximal end of the tracking unit. Housed within the coupler recess may be a drive shaft to drive train coupling assembly. In some embodiments, a magnetic coupler is also provided. In one particular embodiment, the magnetic coupler may comprise a drive shaft connector having a first magnet recess for receiving and magnetically engaging one or more magnets, as well as a plurality of anti-slip cogs. A complementary drive train connector, also having a plurality of anti-slip cogs, may have one or more magnets fixedly connected to drive train connector recess. Drive train connector may further comprise a guide tube, which passes through complementary central apertures of a drive train connector and magnet to extend beyond the distal face of magnet. The guide tube may serve to align and guide the drive shaft connector to properly seat and releasably engage magnet of the drive train connector. The drive shaft connector may be provided with a central aperture for receiving the guide tube, thereby aligning the drive shaft connector with the drive train connector and maintaining a concentric arrangement.

In one embodiment, the drive shaft connector may releasably engage the drive train connector by passing the guide tube through a central aperture of the drive shaft connector and magnetically adhering to the magnet such that the anti-slip cogs are offset and engaged. In operation, rotational movement may be imparted to the drive train by any conventional drive system whereby drive train connector transfers rotational movement to the drive shaft connector by engaging complementary anti-slip cogs on each connector. The drive shaft may be fixedly connected to the drive shaft connector by any conventional methods, such as welding laser welding, soldering, brazing, adhesive bonds and the like. Rotational movement imparted to the magnetic coupler assembly by the drive train is effectively transferred to the drive shaft and the cutter assembly. The magnetic coupler is designed to accommodate the guide wire. The drive train and all distal components may be provided with a central aperture to receive the guide wire, thereby permitting free axial translation of guide wire through the entire system.

Some embodiments of the present invention may include additional features, such as aspiration and/or infusion portals, by which aspirate may be removed from and infusion materials may be introduced into various catheter systems. For example, a wide variety of "quick-connect" devices are well known in the art and may be used in the present invention and may also be adapted for specific use within the removal system. The connecting devices may provide a fluid-tight seal. For example, a connector may form a fluid-tight seal with a coupler recess of the motor assembly housing, which may be further connected to one or more catheters and/or sheaths of the present invention. This design, and any similar variations, may enable the operator to quickly and efficiently switch components of the present invention.

A conduit for aspirate may be integrated into the cutter assembly drive shaft by bonding or shrinking a polymer onto the outer and/or inner surface(s) of the coil drive shaft. TEFLON® brand polytetrafluoroethylene (by e.i. DuPont De Nemours and Company Corporation located in Wilmington, Del.) may be an especially useful polymer for sealing the cutter assembly drive shaft. For many applications of the material removal system of the present invention, a non-compressible multi-filar metallic coil drive shaft without an integrated aspirate conduit may be used. The drive shaft may also have one or more conduit(s) for aspiration and/or infusion being provided internally or externally coaxial with the drive shaft, or a bi-axial conduit. A hollow and flexible drive shaft may be constructed from materials that provide enhanced system flexibility and guidance properties.

Figure 21:
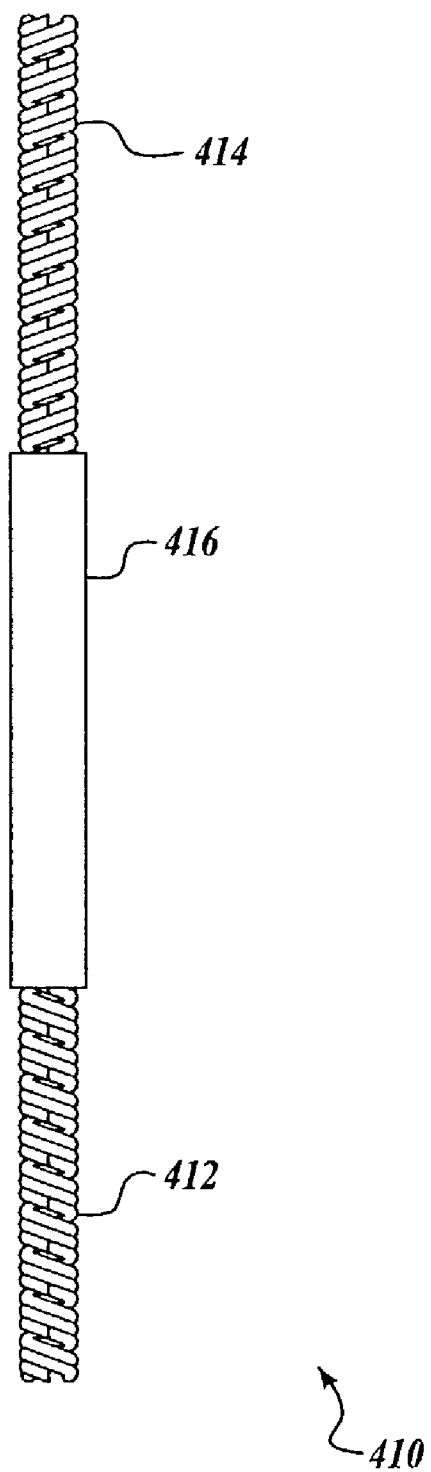
FIG. 21 shows a drive shaft of the present invention having right-lay and left-lay helical configuration.

In one embodiment of the present invention, a self-dampening drive shaft having a "multi-helical" design is provided, herein referred to as a multi-helical drive shaft or simply as a drive shaft. It is desired to make the drive shaft lengthwise so that no unusual loading of the distal cutter system occurs regardless of the direction of the rotation. Depending upon the "lay" of the helical structure and the direction of rotation, helical drive shafts undergo transitory expansion or contraction caused by unwinding or cinching of the helical structure in response to the applied torque, resulting in potential axial loading of the cutting device bearing system. As shown in FIG. 21, multi-helical drive shaft 410 has adjoining sections of "left-lay" and "right-lay" helical configurations 412 and 414, respectively, and each section may be of substantially equivalent length. The "left-lay" and "right-lay" sections 412 and 414 may be arranged along the longitudinal axis of multi-helical drive shaft 410 in any operable configuration, such as, but not limited to, essentially half the drive shaft length being one continuous length of one lay and the remaining substantially equal length being one continuous lengthy of opposite lay; or a plurality of alternating sections of opposite lay sections of any length, such that, in sum, the multi-helical drive shaft is substantially half left-lay and half right-lay.

A multi-helical drive shaft having adjoining lengths of oppositely wound helical coils dampens the movement of adjoining, counterpart section(s). For example, upon counterclockwise rotation, left-lay coiled section(s) of the drive tend to unwind, causing axial displacement in the distal direction, while the right-lay section(s) of the drive shaft will tend to contract, causing axial displacement in the proximal direction. The combined opposing forces and actions effectively cancel the axial movement of each respective section, resulting in negligible axial loading of the distal expandable cutter. The multihelical drive shaft may have any number of opposite-lay sections, provided that opposite-lay sections are properly matched to effectively dampen the axial movement. The opposite lay coils 412 and 414 may be joined together directly, or, as shown in FIG. 21, by means of a fixed connection to a conventional coupler 416 interposed between the coils. Such fixed connections may be provided, for example, by welding, soldering, brazing, adhesives and the like.

The cutter assembly may comprise one or more cutters and one or more distinct types of cutter elements. For example, a dual cutter configuration provide a distal, fixed diameter cutter and a proximal, adjustable diameter cutter. As described in greater detail below, one embodiment of material removal system of the present invention has the ability to remove material from the interior of a lumen, such as a blood vessel or gastro-intestinal lumen, in a two-step process using an expandable cutter assembly. In some methods of using a dual cutter assembly, the cutter assembly is rotated and advanced to remove occlusive material in an initial "pilot pass" in which the distal, fixed diameter cutter is the primary cutter, and the proximal, expandable cutter is in a smaller diameter condition. Following one or more pilot passes, the proximal, adjustable diameter cutter may be adjusted to a larger diameter condition and the dual cutter assembly may be advanced so that the adjustable diameter cutter, in its expanded condition, cuts an even larger volume of occlusive material. Debris and fluids are usually removed from the site, such as by aspiration. Following removal of desired materials, the proximal, adjustable diameter cutter may be adjusted to a smaller diameter condition and the cutter assembly may be withdrawn from the site. This method, using the material removal system of the present invention, obviates the need for the operator to remove and replace, or interchange, cutter assemblies during a material removal operation to provide cutters having different diameters and material removal capabilities.

An enlarged depiction of one example of a cutter assembly is shown in FIG. 1 having a cutter assembly housing 46 provided at distal end of guiding catheter 40 or primary sheath. In one embodiment, the cutter assembly housing 46 may be provided as a continuous, enlarged section of guiding catheter 40 or a primary sheath that accommodates cutter assembly 42. For example, the hollow interior of cutter housing 46 defines an interior space 47 in which the cutter assembly 42 resides when axially retracted in a proximal direction. Interior space 47 of expandable cutter housing 46 may be continuous with the lumen of a primary sheath or the lumen of guiding catheter 40, creating a conduit for the flow of various fluids during aspiration and/or infusion. In another embodiment, the distal end of a primary sheath or the guiding catheter is operably connected to a flared coupling that serves as a cutter assembly housing.

The cutter assembly of the present removal system may be any of a variety of devices having one or more hard and/or sharp cutting surfaces for cutting, fragmentizing, pulverizing, ablating, scraping, grinding or otherwise reducing the size of and/or separating occlusive matter from beneficial matter, such as the walls of a blood vessel, in proximity to the occlusive material. For example, the cutting surfaces may include one or a combination of blade(s), spring(s), metallic or ceramic surfaces having an edge and/or an abrasive surface. Abrasive surfaces may be provided by affixing fine and hard materials, such as diamond grit, etc., to cutting surfaces. The cutter assembly may have blades that are chamfered at one or both of their proximal and distal ends to render them atraumatic to resilient beneficial tissue.

As illustrated in FIGS. 2 and 3, a distal end of drive shaft 25 may be fixedly connected to the cutter assembly, such as an expandable cutter assembly 42. One embodiment of expandable cutter assembly 42 may be a dual cutter assembly comprising a proximal bushing 150, an adjustable cutter housing a central block 152 and a plurality of cutting members 154, a fixed diameter distal burr 156 and an assembly tube 158.

Some exemplary materials for the components of the cutter assembly include metals, metal alloys and ceramics and cermet materials, such as but not limited to, various types of stainless steels, such as series 300 and/or 400, vanadium steel, nickel-titanium, titanium, titanium-containing metals and oxide ceramics. In general, cutter blades are constructed from hard materials and may be treated to impart greater hardness. Cutter blades constructed from a material that is harder than the materials used to construct stents are generally provided. Cutter assemblies of the present invention and the accompanying drives, catheter assemblies, etc., may be constructed having various sizes and configurations to accommodate different material removal applications. For example, expandable cutter assemblies may be provided in several diameters, ranging from less than 2 mm to 5 mm or more. In particular, the expandable cutter assembly may have a contracted diameter/ expanded diameter of 2.25 mm/2.75 mm, 2 mm/2.75 mm and/or 1.5 mm/2.0 mm, or the like.

In the specific embodiment illustrated in FIG. 2, a hollow flexible conduit catheter 94 is coaxially disposed within the lumen of a primary sheath. Conduit catheter 94 may be constructed from plastic such as polyvinyl chloride (PVC), TEFLON® brand polytetrafluoroethylene, Nylon or another polymer, or from a helical metal spring wire encased in a suitable polymer to provide a sealed conduit. Conduit catheter 94 may provide a conduit for aspiration and have sufficient structural integrity to withstand the internal vacuum pressure during aspiration, as well as sufficient flexibility to permit guidance and axial movement of the cutter assembly in an atraumatic manner. In some embodiments, conduit catheter 94 is a coiled metallic catheter 106 having a tightly associated flexible outer sheath 108, such as a TEFLON® sheath which has been "shrink-wrapped" onto the outer surface of the coiled metallic catheter. The present invention may also include other suitable materials for encasing the stainless steel coiled catheter, such as any flexible, biocompatible plastic or synthetic material. A sheathing layer may also be applied using techniques other than heat shrinking, such as, but not limited to, plastic extrusion techniques. For example, according to some embodiments, conduit catheter 94 has an outer diameter of from about 0.045 to 0.060 inch and an inner diameter of from about 0.035 to 0.050 inch. The lumen formed between conduit catheter 94 and drive shaft 25 usually serves as a conduit for fluids and particulates during aspiration and perfusion.

A distal end 100 of conduit catheter 94 is fixedly connected to a proximal section 102 of a first slip seal/bearing assembly 104. Slip seal/bearing assembly 104 is a mechanism for coupling conduit catheter 94 to expandable cutter assembly 42, while permitting free rotation of cutter assembly 42 around a central axis and forming a fluid-tight junction between conduit catheter 94 and cutter assembly 42. Outer sheath 108 of conduit catheter 94 extends to partially cover the outer wall of the proximal section of slip seal/bearing assembly 104. A distal section 110 of first slip seal/bearing assembly 104 is in close association with the collar section 112 of proximal bushing 150, thereby forming the slip seal/bearing junction 104. Collar section 112 of proximal bushing 150 is continuous with body section 118 of proximal bushing 150. Proximal bushing 150 has an axially-aligned central aperture 114, which enlarges at collar section 112 to form a proximal bushing conduit 116. The axially-aligned central aperture 114 receives assembly tube 158. Proximal bushing 150 also possesses a first series of receiving apertures 120 radially arranged around central aperture 114 for receiving proximal end 122 of rod section 124 of cutting members 154. The present invention contemplates proximal bushings having various configurations, such as but not limited to, a bushing having raised ridges that act as a cutting or grinding burr for removing material when the cutter assembly is operated in a retrograde axial direction.

As shown in FIGS. 3 and 4, an expandable type of cutting assembly has cutting members 154, i.e. blades, which may comprise a rod section 124, having a proximal end 122 and a distal end 126. Along the middle portion of each rod section, a blade 128 having a beveled edge 130 for cutting may be mounted. It is understood that the beveled edge 130 of the blade(s) may be of different configuration to facilitate the removal of occlusive material. Rod sections 124 of cutting members 154 may be seated onto central block 152.

Central block 152 may support a plurality of cutting members 154 and may provide a central lumen 136 for receiving assembly tube 158. Central block 152, having a proximal 132 and a distal 134 end, may also serve as a control mechanism for the axial rotation of cutting members 154, which is explained in detail below. Central block 152 often incorporates a plurality of raised spines 138 tangentially arranged around its central axis. Raised spines 138 may have a support face 140 and a stop face 142. The junction between raised spines 138 forms a seat for receiving rod sections 124 of cutting members 154. A proximal end 132 of central block 152 may be permanently fixed to a distal face 144 of proximal bushing 150 using any conventional means, including but not limited to, welds of all types, mechanical attachments and adhesives.

In some embodiments of the present invention, and as depicted in the accompanying drawings, six cutting members 154 are mounted on a central block configured to support six cutting members. Cutting members 154 are seated in the junctions of raised spines 138 of central block 152, with the blade section 128 of each respective cutting member 154 contacting the support face 140 of the corresponding raised spine 138 of central block 152. The distal end 126 of each rod section 124 of cutting members 154 extends distally beyond the distal end 134 of central block 152 to engage the proximal face 160 of a distal cutter 156 having a fixed diameter.

As shown in FIGS. 1, 2, 3, 5 and 6, the fixed diameter distal cutter 156 typically may have a frusto-conical cross-sectional configuration and a series of raised cutting flutes 148, i.e. blades. The fixed cutter 156 may be provided distally to an adjustable cutter or without another cutter in the cutter assembly.

The raised cutting flutes 148 of fixed cutter 156 and/or the cutting members of an expandable cutter may operate according to the principle of differential cutting and operate to cut, scrape or grind occlusive matter, without damaging other tissues in proximity to the occlusive material, such as internal blood vessel surfaces. In operation, these blades make contact with the vessel wall in order to efficiently remove the target matter along the vessel wall; however, the vessel surface remains undamaged.

The blades may be configured and/or located on the cutter assembly such that they have relatively small blade angles of attack that promote efficient differential cutting. The blade "angle of attack", as referred to herein, is the angle between the leading face of a blade and a tangent to a circle formed by the tips of the blades while the cutter assembly rotates about a central axis, i.e. the longitudinal axis, of the cutter assembly. Angles of attack of differential cutting blades of the present invention are preferably acute. That is, they are less than 90°. The tangent line to the circle formed by the tips of the blades is on a plane that is generally parallel to the longitudinal axis of the cutter assembly, which is also often the longitudinal axis of the catheter coupled to the cutter assembly. Thus, this tangent is not on a plane that extends through the axis of rotation. In some embodiments, the plane of the cutter blades is radial to the axis of the drive shaft. The "angle of attack" is also referred to herein as "blade angle".

Figure 7A:
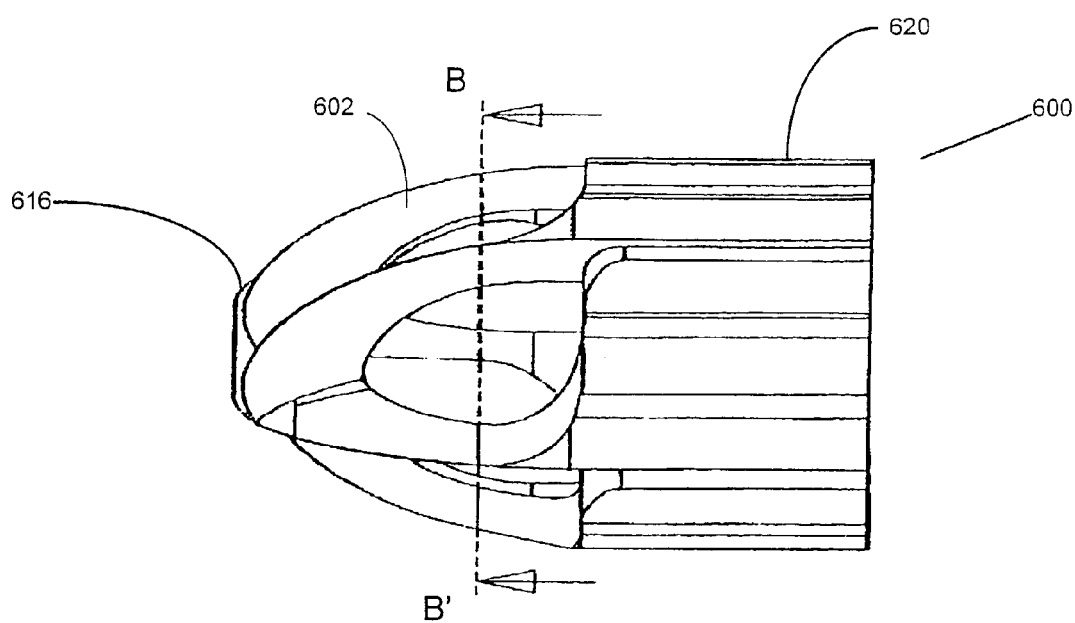
Figure 7B:
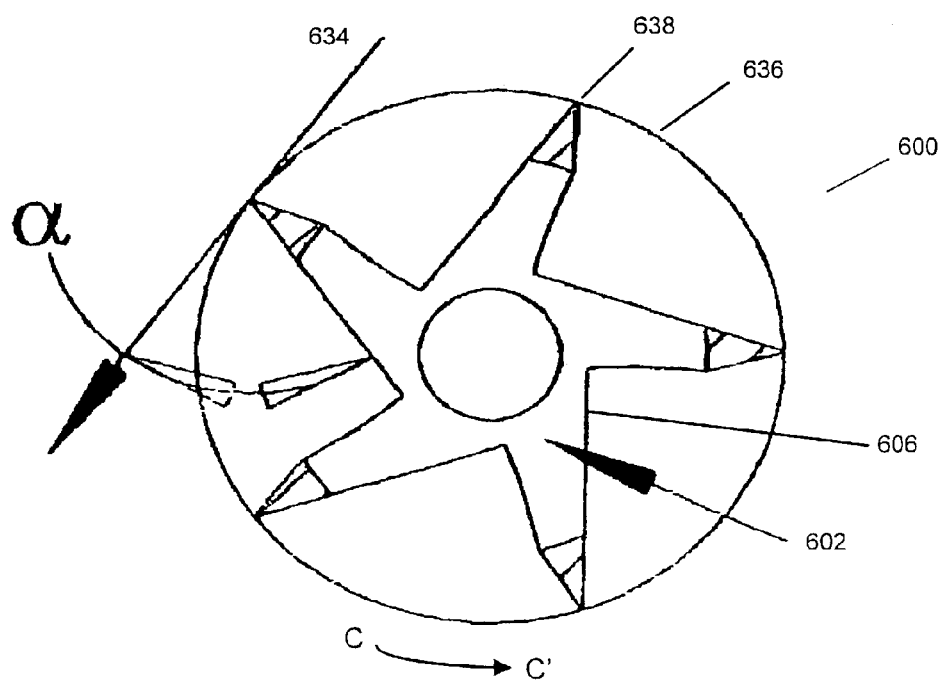

One example of the use of an acute angle of attack for a cutter assembly, according to the present invention, is depicted in FIG. 7B. FIG. 7A depicts a side view of one embodiment of cutter assembly 600. FIG. 7B is a cross-sectional view through line (B to B') of the head of cutter assembly 600 viewed from the proximal to distal ends of the blades. Each of the blades 602 is positioned to form an acute blade angle ($\alpha$). The blade angle ($\alpha$) is defined by the angle of intersection of the surface of a blade's leading face 606 and tangent line 634, which is tangent to a circle 636 formed by the outermost tips 638 of the blades 602. A leading face is a surface of the blade that faces the direction of the rotation and, in use, that contacts the material during cutting in the direction of rotation C to C'. The opposite facing surface on the opposite side of the blade is a trailing face, which is positioned to face the opposite direction of rotation and does not contact the matter when the cutter assembly is rotated in the direction of rotation from C to C'. The tangent line 634 is in a plane to the circumference 636 of the cutter assembly defined by the outer edge of all of the blades at the blade's outermost tip 638.

In the cutter assembly and blade embodiment illustrated in FIG. 7B, both faces of each blade 602 may serve as leading faces, depending on the direction of rotation of the cutter assembly. Both faces of blades 602 form an acute blade angle, defined by the angle of intersection of the surface of the blade's face and a line tangent to a circle formed by the blades tips, and both faces of blades 602 may form cutting surfaces, depending on the direction of rotation of the cutter assembly.

Acute blade angles of cutting assemblies of the present invention should be sufficient to permit differential cutting and effectively separate the undesirable matter from the beneficial material in proximity to the undesired matter. Oftentimes, the use of a smaller, i.e. more acute, blade angle results in a scraping action of the cutter assembly rather than a slicing action, which is observed with larger angles, and particularly blade angles greater than 90°. Preferred blade angles for differential cutting purposes are typically acute, for example, less than or equal to 90°. Acute blade angles are preferably greater than 10° and less than 90°, and also may be greater than about 30° or 45° or 60° and less than 90°. In still other embodiments, the blade angle may be between about 45° to less than or equal to about 75°, and in another embodiment is less than 70°.

Figure 7C:
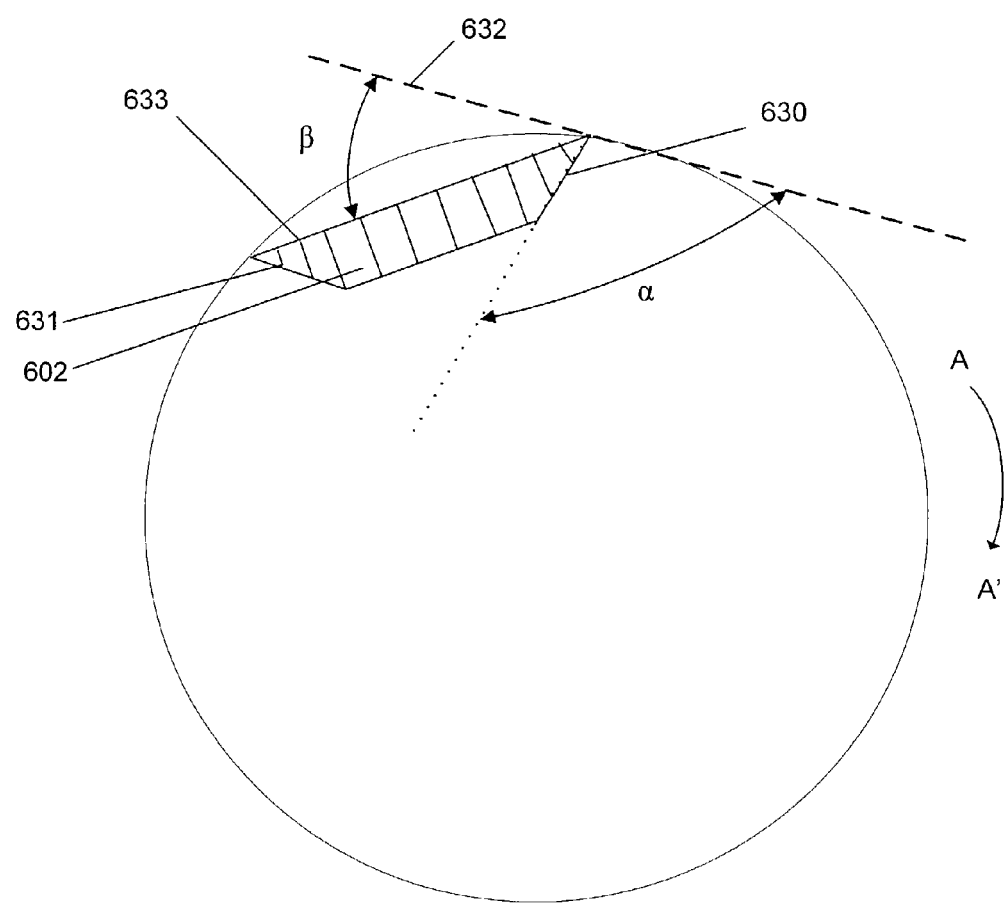

An example of a prior art cutting device that has an obtuse blade angle is shown in FIG. 7C, wherein cutting movement is in a direction A to A'. The blade 602 has a leading edge 630, a trailing edge 631 and a flat outer face 633. The blade attacks the tissue at a tangent 632 to a circle. In some embodiments, the tangent may represent a tissue surface and the circle may represent a round lumen. In any case, although an acute angle β is formed between the outer face 633 and tangent 632, the blade angle of attack a, as defined herein, between the leading edge 630 and tangent 632 is obtuse. It is this larger obtuse blade angle, e.g. larger than 90 degrees, that result in an increasingly aggressive cutter assembly that is more likely to cut healthy tissue.

The larger, obtuse blade angles used in prior devices also may require the use of thinner and less robust blades. It has been found through the present invention, however, that a an acute blade angle, e.g. less than 90°, provides safe separation of undesired from desired material, particularly in applications where the undesired material comprises as calcified matter, e.g. bone, atherosclerotic material, thrombus, and similar materials. The acute blade angles used in cutter assemblies of the present invention also do not harm healthy tissue, such as skin, healthy vessel walls, and the like. This enhanced differential cutting capability also allows a fewer number of blades to be used in a cutter assembly than the number that may be required by other cutting devices having larger blade angles. The presence of fewer blades may also allow for larger ports to be provided between the blades. In some instances the cutter assembly has the ability to rotate in both clockwise and counterclockwise directions.

The blade angle may be optimized to provide the desired aggressiveness when rotated in one direction, and likewise when rotated in the opposite direction. Furthermore, the exemplary cutting assemblies with blade arrangements described herein are not intended to limit the scope of cutting assemblies and arrangements of blades that may be employed with the inventive blade angles for differential cutting. It is understood that other embodiments of cutting assemblies, which may have blades arranged in various fashions, and that have acute blade angles for differential cutting are within the scope of the invention.

In one embodiment, where the cutter assembly changes directions of rotation to cut, e.g. clockwise to counterclockwise, or visa-versa, the leading face and trailing face of the blade may also switch sides of the blade such that the leading face always faces the direction of rotation. In this embodiment, opposing faces of a blade may have a profile to provide for an acute blade angle for differential cutting. Further, in this case, these opposing sides may have the same profile such that they provide the same blade angle, or the profiles may be different such that the blade angles of each side are different. In addition, where for a multiple cutter assembly having an expandable cutter and fixed cutter, the blades of individual cutters may have opposite sides of the blades of each cutter serving as the leading faces, where the expandable cutter rotates in one direction to cut and the fixed cutter rotates in the opposite direction to cut.

Figure 8A:
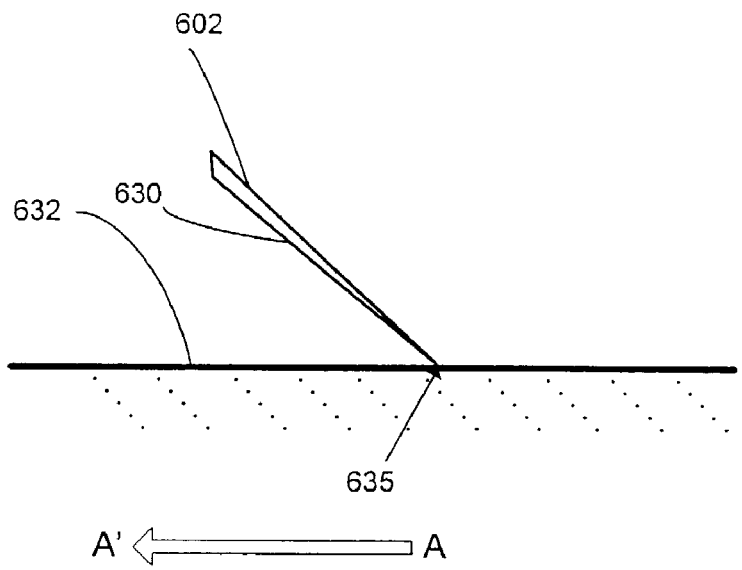

One example of the use of a cutter assembly in approaching a tissue surface with an acute angle of attack, according to the present invention, is depicted in FIG. 8A. The cutting head is rotated such that each blade sequentially contacts the surface of the target matter and usually also contacts the support surface at a blade contact point 635. The leading surface 630 of the blade 602 takes an acute or narrow approach to the surface 632 of the target matter and/or support surface. The scraping or cutting motion, produced by rotation of the blades, proceeds in a direction A to A' in the direction of the leading face. The support surface that contacts the target matter deforms to reposition out of the way of the blade edge. In this manner, the beneficial material of the supporting surface remains unharmed from the blade even though the blade may move along the surface of the beneficial material.

The dislodged matter may be withdrawn by aspiration through ports of the cutter assembly to remove the matter from the body cavity. Unlike some prior blades that are designed with blade angles relative to the longitudinal plane extending through an attached catheter, e.g. axis of rotation, such that the blades may not abrade the matter close to the surface of beneficial material, e.g. vessel wall, touching the matter to be removed, but rather may cut matter in front of the beneficial material. By contrast, the present invention cutter assembly is designed to contact the beneficial material in order to scrape or cut the matter from the surface of the beneficial material. Still, other prior references describe blades that are placed at large angles, increasing the risk of damaging elastic material.

Figure 8B:
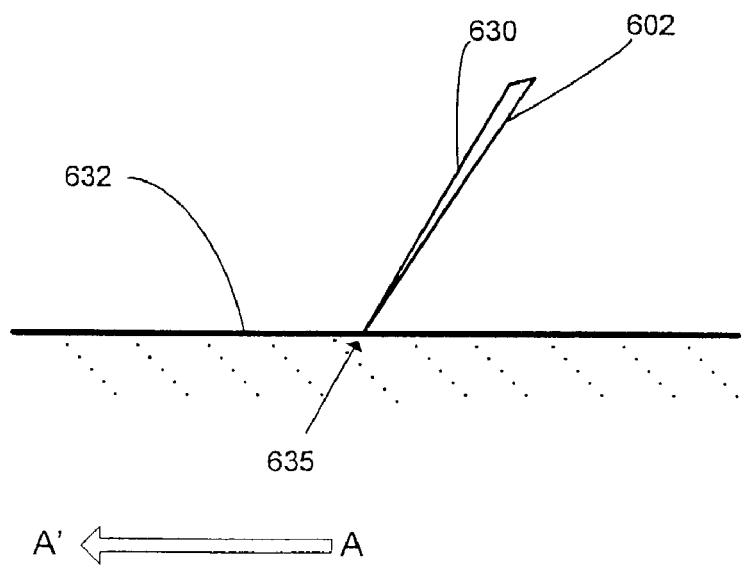

An example of one prior art cutting device is depicted in FIG. 8B, wherein the cutting movement is in a direction A to A'. The blade 602 has a leading face 630 that is positioned with a wide approach to the surface 632, i.e. greater than 90 degrees, to the surface 632. It was previously believed that the blade must be approach a surface at a large angle, similar to a razor's edge, in order to sufficiently abrade matter. However, it has now been found through the present invention that this wide angle approach may cause the blade to incise into the issue surface as well as the overlying unwanted matter. The present advantages of a narrow approach were not previously recognized.

In some embodiments of cutting device, the blades of either one of the cutters or all cutters in a multiple cutter assembly, e.g. a fixed cutter and other cutting members 154, may be designed and arranged to function according to the principle of differential cutting, to preferentially remove occlusive matter while being atraumatic to the more resilient vessel walls. In some embodiments, proximal and distal portions of cutting flutes 148 are chamfered to render them atraumatic.

It is understood that the fixed diameter cutter may be of any suitable configuration, and numerous fixed diameter cutter configurations are known in the art. The dimensions of the fixed cutter vary depending upon the particular application and embodiment but, for intravascular applications, the largest outer diameter of the fixed diameter cutter is generally in the range of 1.5 mm to 2.5 mm.

As shown in FIG. 3, fixed cutter 156 may be provided with a central aperture 146, which defines a surface for mounting assembly tube 158 and receiving the guidewire. A second series of receiving apertures may be present in proximal face 160 of fixed cutter 156. The receiving apertures may be radially arranged around the central lumen, and complementary to the first series of receiving apertures 120 located on distal face 144 of proximal bushing 150. The receiving apertures receive distal end(s) 126 of rod sections 124 of cutting members 154. In certain embodiments of the present invention, the fixed cutter may be fixedly joined by a connection means to the central block. This permanent, fixed connection may be achieved by any conventional means, such as a weld, e.g. a laser-weld, soldering, brazing or an adhesive bond between the distal end 134 of central block 152 and proximal face 160 of fixed cutter 156.

Assembly tube 158 may serve as a connecting means for the cutter assembly 42, as well as a bore for receiving a guidewire and a conduit for fluids and debris during aspiration and/or infusion. Assembly tube 158 may comprise a body section 166, a proximal end 168 and a distal flanged cap section 170 having a central aperture 172 defining guidance passage 174. A proximal end 168 of assembly tube 158 may traverse central aperture 146 of fixed cutter 156, and central lumen 136 of central block 152, and central aperture 144 of proximal bushing 150 to fixedly connect with the distal end of drive shaft 25. Distal cutter 156, central block 152 and proximal bushing 150 may be fixedly joined to the assembly tube by any conventional connection means, such as but not limited, to welds, adhesives and mechanical connection means, such as compression fitting. The components of the cutter assembly may be drawn in and held in tight association by the distal flanged cap section 170 of assembly tube 158.

The present invention often has additional features which permit the aspiration of fluids and small particulates from the vessel lumen, as well as perfusion of liquids, such as physiologically balanced salt solutions, diagnostic or therapeutic substances, and/or contrast media into the intralumenal space in proximity to a material removal site. In general, as illustrated in FIGS. 2 and 3, the inventive device may have a primary aspiration means through the primary sheath, and a secondary aspiration means through a plurality of ports in cutter assembly 42 and lumen 186 formed between flexible conduit catheter 94 and drive shaft 25, which, in some embodiments, is continuous with lumenal space of primary sheath. Proximal end of the primary sheath may be operably connected to a vacuum control unit 18 and may incorporate one or more flow-regulation systems, such as valves, seals, manifolds and the like. Upon actuation of the vacuum assembly and opening of the flow-regulation means, a vacuum may be created in the lumen formed by primary sheath that draws fluids and particulates from the material removal site and deposits fluids and associated debris in an aspirate collection means.

A secondary aspiration and perfusion system is provided using a plurality of ports in cutter assembly 42 to draw fluids and particulate debris through lumen 174 of assembly tube 158, providing a conduit which is continuous with lumen 186 of flexible conduit catheter 94 and a lumen of a primary sheath. As illustrated in FIGS. 2-6, cutter assembly 42 may be provided with a plurality of ports in assembly tube 158, fixed diameter distal cutter 156 and central block 152. Ports 194, 194', etc., in distal cutter 156 communicate with assembly tube ports 196, 196', etc. In some embodiments, distal cutter ports 194, 194', etc. are interspaced circumferentially around the distal cutter 156. Central block 152 may have a first plurality of circumferentially interspaced ports 204, 204', etc., in the distal portion, and a second plurality of circumferentially interspaced block ports 206, 206' etc., in the proximal portion, which may be arranged in a staggered configuration. The first plurality of ports 204, 204', etc. may define a lumen that is in alignment and continuous with the second group of assembly tube ports 198, 198' etc., and the second plurality of ports 206, 206' etc. may define a lumen that is in alignment and continuous with the third group of assembly tube ports 200, 200' etc., such that under vacuum conditions, fluid and particulates flow through cutter ports 194, 194' etc., central block ports 204, 204' and 206, 206' etc. as shown by arrow 208 and 210, respectively. Fluid and particulates may continue to flow through assembly tube lumen 174 to a third group of assembly tube ports 202, 202' etc., to lumen 186 of conduit catheter 94, as shown by arrow 212. The infusion of fluids may be provided by switching to an infusion source and reservoir, and reversing flow so that fluid flows through cutter assembly 42 in a direction opposite that of directional arrows 208 and 210.

Operationally, the intralumenal material removal system is usually introduced into the body by way of a lumen, such as a blood vessel, using techniques that are well known in the art. Typically, an access sheath is employed to access the desired vessel at the point of introduction. Through an installed access sheath, the guiding catheter, which may house the guidewire 11, cutter assembly 42 and other associated components and serve as a delivery vehicle for those components, may be navigated and advanced to the desired site of material removal. In general, the guidewire brake may be released and distal end of guiding catheter 40 may be axially translated to a location proximal to the desired material removal site. Guidance and navigation of guiding catheter and associated cutter assembly may be facilitated by the infusion of fluids, such as contrast media, to monitor the progress of the guiding catheter. The cutter assembly, or sub-components thereof, may be coated with a radiopaque material such as gold, platinum, inks and the like, to render the expandable cutter assembly radioscopically visible and to assist a medical professional in guiding and positioning the cutter assembly relative to an occlusion.

Once the guiding catheter is positioned, the flexible conduit catheter, or other internal catheter, may be extended distally to facilitate placement of the cutter assembly near the occlusion. The distal end of cutter assembly 42 may be positioned at the proximal boundary of the occlusion, whereupon drive system 24 may be actuated and drive shaft 25 and cutter assembly 42 may be rotated. In the use of one embodiment of a dual cutter assembly illustrated in the accompanying figures, particularly in FIGS. 5A and 5B, cutter assembly 42 is often initially rotated in a counter-clockwise direction and advanced so that distal, fixed diameter cutter 156 cuts and abrades the occlusion. Initial rotation of cutter assembly 42, contacting distal cutter 156 with the occlusive material, is capable of removing occlusive material having a cross-sectional area roughly equivalent to the largest outer diameter of distal cutter 156 and diameter central block 152/cutting members 154 assembly in its contracted state. Initial "pilot passes" remove part of the occlusive material and subsequent passes with the cutter assembly in the expanded configuration remove additional material. Of course, alternative embodiments of the present invention may be configured to operate in the opposite rotational direction described above, such that clockwise rotation provides a contracted state and counterclockwise rotation expands the cutter assembly.

As the fixed diameter cutter assembly is rotated and advanced to remove occlusive material, fluid and debris particulates may be aspirated using the primary and secondary aspiration mechanisms described above. It may be desirable to alternate between advancing and retracting cutter assembly 42 to facilitate the aspiration of particulates, especially particulates which are too large to pass through ports 194, 204, 206, etc. in cutter assembly 42. For example, retracting cutter assembly 42 in a retrograde direction (i.e. proximally) within cutter housing 46 of primary sheath 40 during aspiration often creates a laminar-like flow, thereby more effectively drawing fluid and particulates into housing 46 and permitting particulates to be further broken down by the grinding action of the rotating cutter assembly within housing 46. Larger particulates may thus be broken down to a size that can be withdrawn, with fluids, through aspiration ports 194, 204, 206, etc.

Figure 6A:
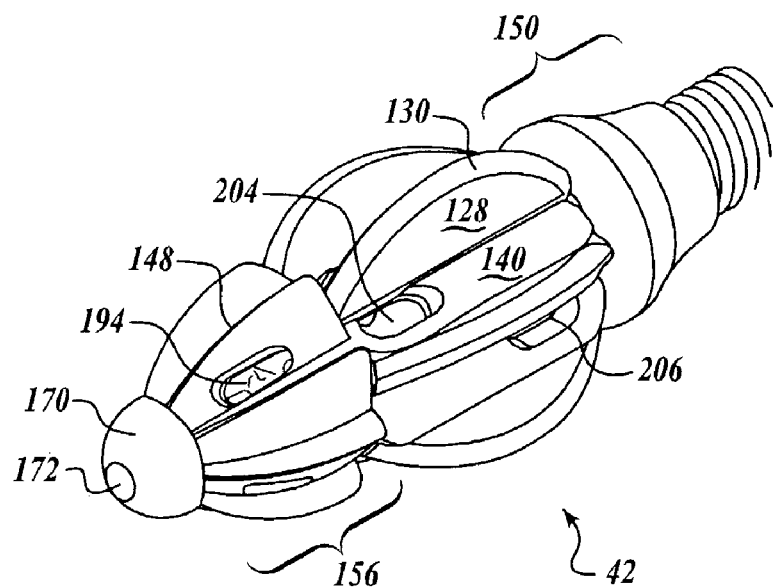
FIG. 6A illustrates an enlarged, perspective view of one embodiment of the dual cutter assembly of FIG. 6A with the cutter assembly in an expanded configuration.
Figure 6B:
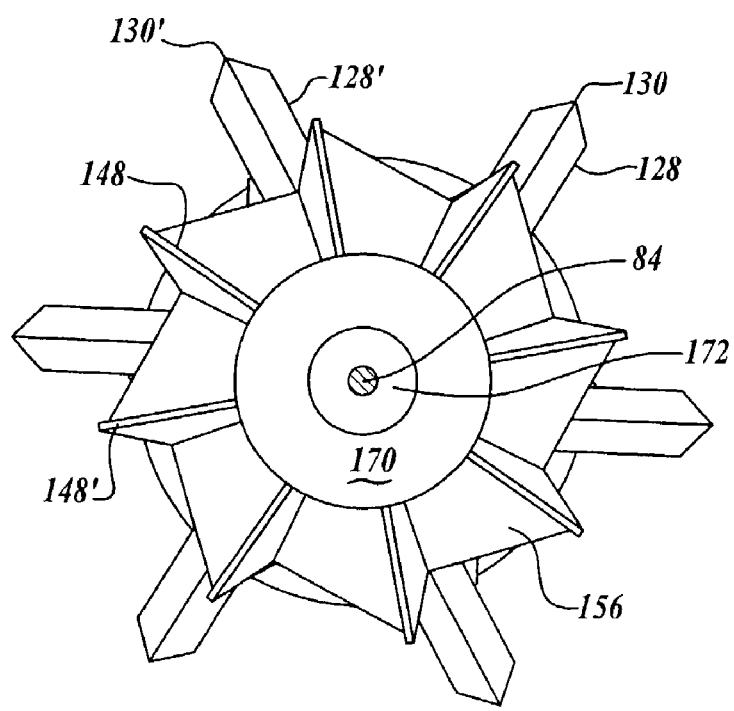
FIG. 6B illustrates an enlarged, front view of one embodiment of the dual cutter assembly of FIG. 6A with the cutter assembly in the expanded configuration.

In further use of a dual cutter assembly, once one or more initial pilot-passes are complete, the expandable cutter assembly may be retracted in a retrograde direction to the proximal boundary of the occlusion and the direction of rotation of the expandable cutter assembly may be reversed. Reversing the direction of rotation from a counterclockwise direction to a clockwise direction causes cutting members 154 of expandable cutter assembly to open to an expanded configuration, as illustrated in FIGS. 6A and 6B. Specifically, as the expandable cutter assembly 42 is rotated in a clockwise direction, centrifugal forces of rotation combine with hydrodynamic and frictional forces between the surrounding fluid within the lumen and blades 128 of cutting members 154, cause cutting members 154 to rotate around a central axis, as defined by rod sections 124 of cutting members 154. Cutting members 154 may rotate freely within the first receiving apertures 120 and second receiving apertures 164 in proximal bushing 150 and distal cutter 156, respectively. Cutting members 154 rotate from a tangential orientation, in which blades 128 are in contact with the respective support faces 140 of raised spines 138 of central block 152 (i.e., the contracted configuration) to a radial orientation in which blades 128 of cutting members 154 are in contact with stop faces 142 of raised spines 138 of central block 152 (i.e., the expanded configuration). Stop faces 142 of raised spines 138 check the rotational movement of the cutting members 154, as well as provide support to blades 128 of cutting members 154 while in the expanded configuration during operation. Movement of the cutting members to the radial configuration increases the overall outer diameter of the cutter assembly. For example, in select embodiments, the outer diameter of the expandable cutter assembly in the contracted configuration may be approximately 2 mm, and the cutter assembly may be expandable to an outer diameter of approximately 2.75 mm. As previously described, the present invention may be designed in a wide range of sizes to accommodate various applications.

While in the expanded configuration, the expandable cutter assembly may be axially translated along guidewire 11 to retrace the pilot-pass made through the occlusion, whereupon beveled edges 130 of cutting members 154 engage the occlusive material, removing a larger volume of occlusive material. As previously described, aspiration may be provided throughout the operation of the expandable cutter assembly to effectively remove the particulate debris dislodged during cutting and grinding of the occlusive material.

After sufficient occlusive material has been removed, the expandable cutter assembly may be contracted by engaging the drive system to rotate cutter assembly 42 in the opposite direction, i.e. for the purpose of this example, in a clockwise direction. The centrifugal, hydrodynamic and frictional forces may again act on blades 128 of cutting members 154, causing the cutting members to rotate around a central axis, as defined by rod sections 124 of cutting members 154. Cutting members 154 rotate from a radial orientation, in which blades 128 of cutting members 154 are in contact with stop faces 142 of raised spines 138 of central block 152 (i.e., the expanded configuration) to a tangential position in which blades 128 are in contact with the respective support faces 140 of raised spines 138 of central block 152. Support faces 140 of raised spines 138 stop the rotational movement of the cutting members 154, as well as provide support to blades 128 of cutting members 154 while in the contracted configuration. While in its contracted state, the cutter assembly 42 may be retracted into the primary sheath or guiding catheter for removal from the body or further advanced distally along guidewire 11 to perform additional operations. FIGS. 6 and 9-11 present one embodiment of the present invention. Wherever appropriate, the same reference numbers have been employed to describe the same or similar elements. In general, the dimensions, materials, method of operation and the like used to describe the previous embodiment apply equally to all embodiments presented herein unless stated otherwise.

FIG. 9 depicts an alternative embodiment of a dual cutter assembly according to the present invention comprising at least one flexible conduit catheter 94' in which drive shaft 25, such as a multi-helical drive shaft, runs coaxially within its internal lumen. A proximal encasement 340 may fixedly connect flexible conduit catheter 94' to a secondary segment of flexible conduit catheter 342, which in turn may fixedly connected to a distal encasement 344. Distal encasement 344 may form a slip-bearing fitting with a proximal cap 346, thereby permitting free rotation of drive shaft 25 and cutter assembly 42' within coiled metallic catheter. As with previous embodiments, cutter assembly 42' may comprise a central block 152', a fixed diameter distal cutter 156' and a plurality of cutting members 154'.

Figure 11:
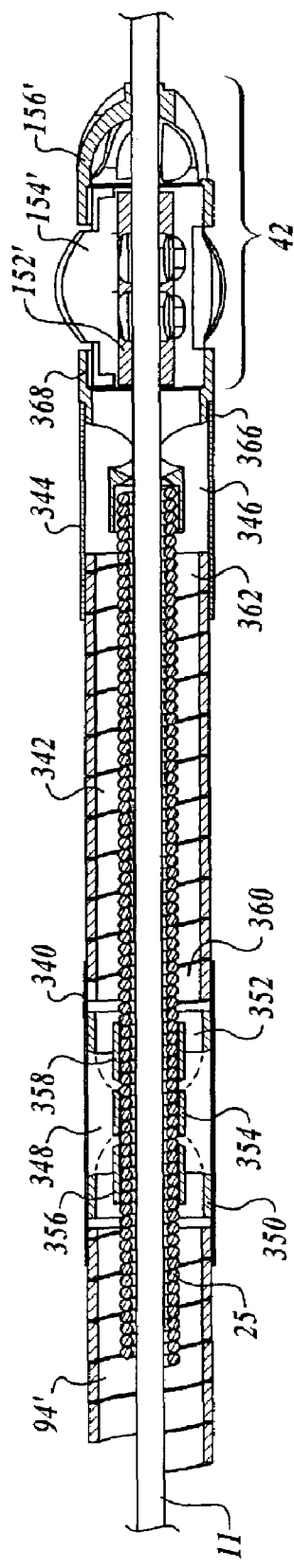
FIG. 11 provides a cross-sectional perspective of an alternative embodiment of the present invention.

As illustrated in FIGS. 10 and 11, drive shaft 25 may be provided with retainer assembly or mechanism 338 for interconnecting drive shaft 25 and flexible conduit catheter 94'. Any conventional assemblies or mechanisms may be utilized, such as a retainer 348 having a first end 350 fixedly connected to flexible conduit catheter 94' and a second end 352 fixedly connected to a first end 360 of secondary segment of flexible conduit catheter 342, by any conventional methods, such as by welding, laser-welding, soldering, brazing, adhesive bonds and the like. Retainer 348 may operate in conjunction with one or more thrust bearings to facilitate cooperative axial translation of drive shaft 25 and flexible conduit catheter 94' in either an antegrade or retrograde direction. A first thrust bearing 356 may fixedly connected to drive shaft 25 proximal to center section of retainer 354, and a second thrust bearing 358 may fixedly connected to drive shaft 25 distal to center section of retainer 354 in such a manner as to bring first 356 and second 358 thrust bearings in close or tight association with center section 354 of retainer 348. Drive shaft 25 may freely rotate within central aperture of retainer 348. Retainer assembly may be enveloped by some tubular sheath, such as proximal encasement 340 to add additional strength and provide a relatively smooth profile to flexible conduit catheter 94'.

Notably, retainer assembly 338 and proximal encasement 340 may be located an operable distance from cutter assembly 42'. "Operable distance," as used herein, is defined as a distance which permits secondary segment of flexible conduit catheter 342 and associated cutter assembly 42' to retain sufficient flexibility to effectively maneuver within intralumenal spaces, particularly along curved, arched and/or branched sections of lumenal bodies. The distance between retainer assembly 338/proximal encasement 340 and distal cutter assembly 42' may be less than 1 cm to over 20 cm.

Cutter assembly 42' may be fixedly connected to drive shaft 25 while permitting free rotation within flexible conduit catheter 94'. Drive shaft 25 may be fixedly connected to a proximal cap 346, which has a distal flange section 366 fixedly connected central block 152'. This arrangement transfers rotational movement from drive shaft 25 to cutter assembly 42'. Proximal cap 346 may be provided with a central aperture for receiving guide wire 11, and a number of cut-away sections to create one or more accesses continuous with the lumenal space within all sections of flexible conduit catheter 342, 94'. This lumenal space serves as a conduit for aspiration and infusion materials and is continuous with the various ports of cutter assembly 42'. A slip seal/bearing assembly 368 may be created at the connection between distal encasement and flange section of proximal cap 366 thereby permitting free rotation of drive shaft 25, proximal cap 346 and cutter assembly 42' within flexible conduit catheter 94', 342 without imparting rotational movement to flexible conduit catheter 94', 342, which minimizes unnecessary trauma to the surrounding tissues.

Figure 12:
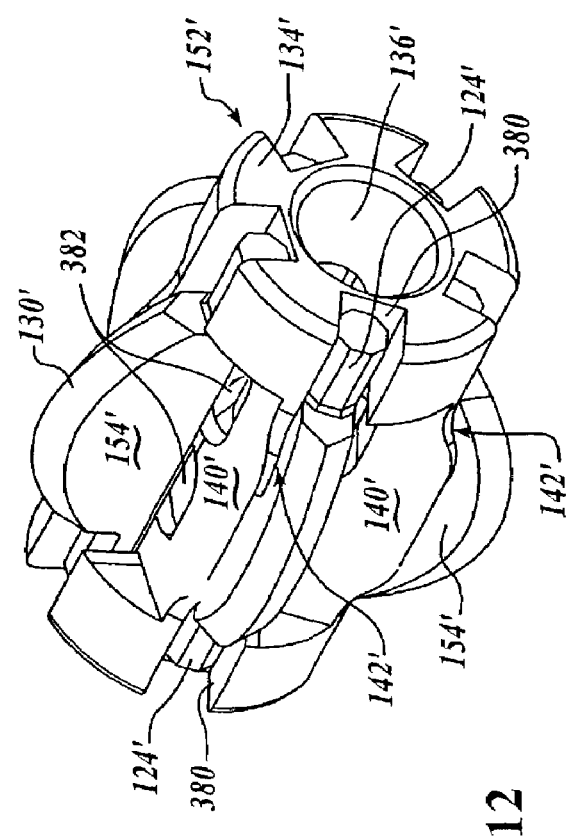
FIG. 12 shows an embodiment of a expandable cutter highlighting the central block and cutting members assembly.

The embodiments depicted in FIGS. 9-11 have a number of uniquely distinguishing features. As shown in FIGS. 10, 11 and 12, central block 152' may be fitted with any suitable number of cutting members 154', such as 8 or less. This embodiment shows a central block having 5 cutting members, but, depending upon the application and overall dimensions of the cutter assembly, greater or fewer than 5 cutting elements may be employed. FIG. 12 shows central block 152' having a plurality of receiving slots 380 for receiving rod sections 124' of cutting members 154'. Cutting members 154' may be formed from interconnected rod and blade members, or often machined from one integral piece. As with the previous embodiment, cutting members 154' are provided with beveled edges 130', such that the principles of differential cutting apply. It is understood that any suitable differential cutting angle may be utilized for beveled edge 130' in addition to those depicted in the figures. A central aperture 136' may be provided running along the longitudinal axis of central block 152' to permit free axial translation of guide wire 11 and/or other components, as well as serve as a conduit for aspiration and infusion. A plurality of ports 382 may be provided in central block 152' which are continuous with central aperture 136' and lumen of flexible conduit catheter 342, 94', further providing aspiration capabilities to cutter assembly 42'. This particular embodiment provides a greater number of ports 382 in central block 152', thereby increasing aspiration and infusion efficiency. Distal face 134' of central block 152' may be fixedly connected to proximal face 160' of fixed diameter distal cutter 156' by any conventional methods, such as by welding, e.g. laser welding, soldering, brazing, adhesive bonds and the like.

One aspect of the present removal system relates to improved cutting assemblies and includes a cutter assembly that is especially useful in differential cutting. In some embodiments of the present invention, multiple blades are provided to dislodge and/or ablate the intracorporeal matter. These blades may be positioned at acute blade angles for attack, e.g. less than 90 degrees, for enhanced differential cutting abilities. In addition, one or more port(s) may be included as large openings between the blades to permit highly efficient removal of debris. The position, shape and/or size of the blades and ports promote highly efficient differential cutting and debris removal.

Figure 13A:
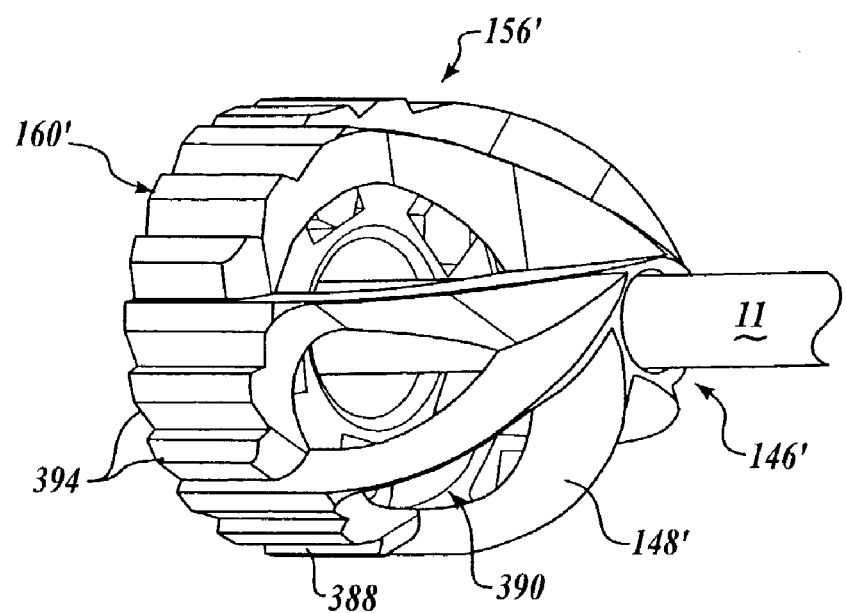
FIG. 13A illustrates a side view of another embodiment of a fixed diameter distal cutter, and FIG. 13B provides a front perspective of the fixed diameter distal cutter illustrated in FIG. 13A.
Figure 13B:
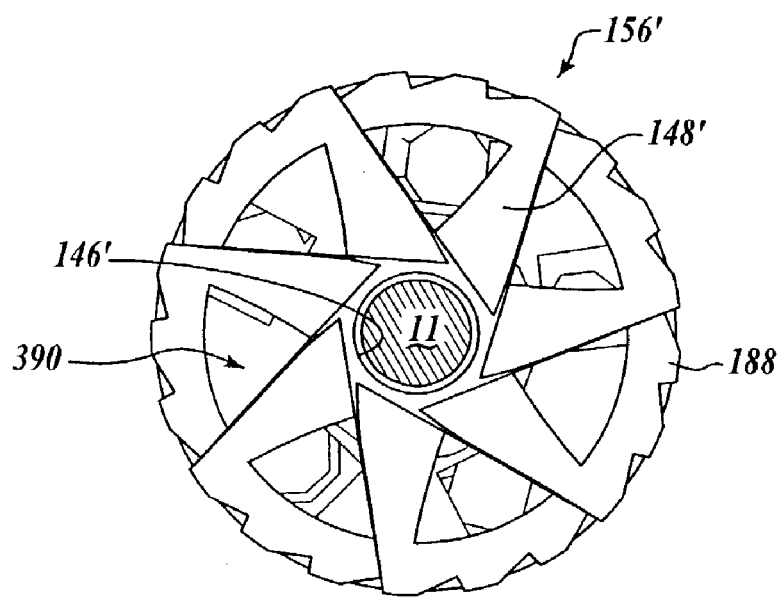

As more clearly illustrated in FIGS. 13A and 13B, cutter 156' may be generally of tapered, oblong, conical or frusto-conical design, or any suitably balanced configuration, and is usually provided with a plurality of raised "arch-like" cutting flutes or blades 148' radiating from central aperture 146' to body 388 of cutter assembly 156'. As with all cutting members, blades and cutters described herein, this particular embodiment of a cutter also operates by differential cutting. Additionally, proximal and distal aspects of cutting flutes or blades 148' may be chamfered to render them atraumatic.

As shown in FIGS. 13A and 13B, cutter assembly 156' may be provided with a plurality of port-like cutouts for aspiration and infusion. In the context of this particular embodiment, port-like cutouts may also be referred to as ports. Each pair of cutting flutes 148' may be cut away to provide an aspiration cutout 390, which form an internal cavity that is continuous with central aperture 136' of central block. This arrangement may provide an aspiration and infusion conduit to the most distal end of the cutter assembly. The design and arrangement of cutting flutes 148', and aspiration cutouts 390 create an open configuration providing substantially maximal cutout surface area, which allow a greater volume of material to be aspirated from the situs of operation. In addition, cutter assembly 156' may have any sort of cutting and/or grinding elements 394 associated with body 388 of cutter assembly 156' to further facilitate removal of occlusive material.

Figure 14:
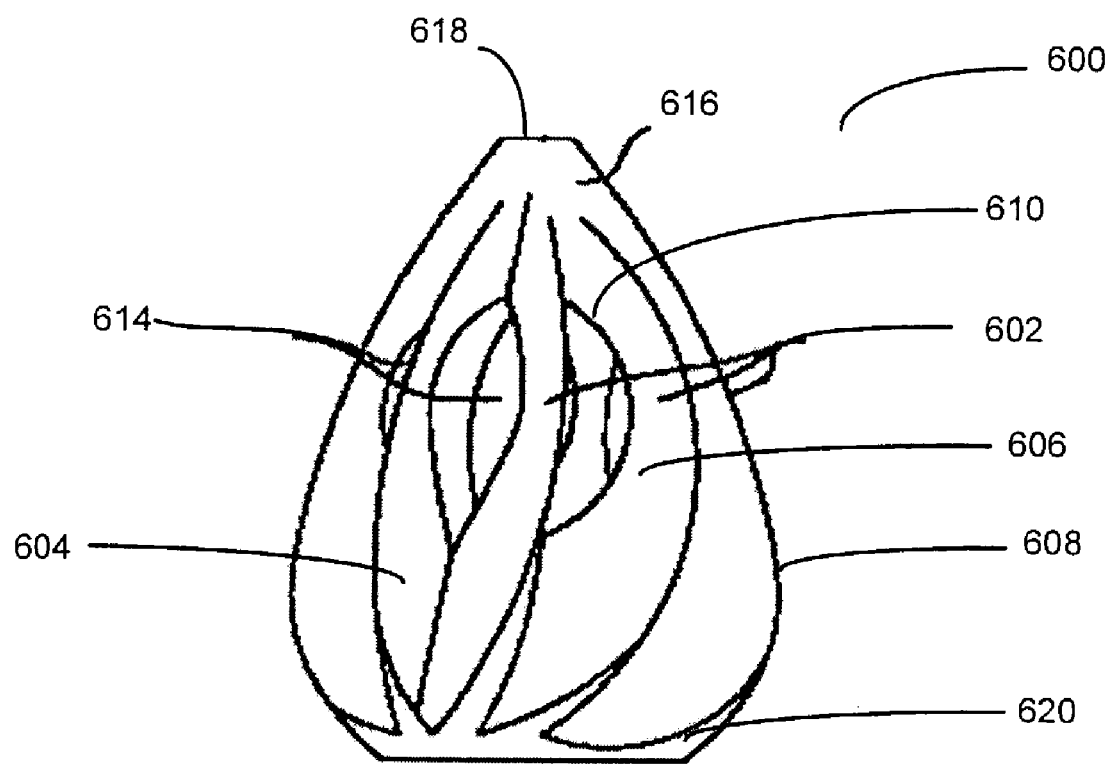
FIG. 14 is a schematic diagram illustrating an external view of a cutter assembly having large ports between blades according to one embodiment of the present invention.

Another example of one such a cutter assembly that is designed for differential cutting is depicted in FIG. 14. Cutter assembly 600 comprises a plurality of blades 602 arranged in a radially symmetrical configuration to ablate. In one embodiment, as shown, the blades extend along a plane that is generally parallel to the center of axis of the cutter assembly. Ports 614 are defined, at least in part, by the gaps between the blades 602. The ports open from the exterior of the cutter assembly and extend to the internal head, to receive ablated intracorporeal matter and/or fluid. The gap may be formed between a blade facing surface 604 on each blade presented at least substantially in front of and spaced apart from an adjacent and opposing blade's facing surface, such as leading face 606.

The cutter assembly may further have a distal tip 616 on its distal end and on its opposite end, a proximal end 620. In some embodiments of cutter assembly 600, the distal tip 616 may have a central bore 618 through which a guide wire may be slidably engageable. In other embodiments, no guide wire is used and the distal tip does not accommodate a guide wire.

Typically, the blade 602 is also provided with an outer surface 608 for contacting and cutting the matter to be removed. The outer surface may be, for example, a sharp edge. In one embodiment, the outer surface may additionally have an abrasive or cutting material, e.g. diamond grit, bonded to it. On the side opposite of the outer surface the blade may also have an inner surface 610 facing an internal cavity within the cutter assembly.

The blade may be composed of any material sufficiently durable to ablate the matter of interest and usually is a hard material. For example, the blade may comprise stainless steel, such as series 300 and/or 400, vanadium steel, nickel-titanium, titanium-containing metals, oxide ceramics, etc. Typically, softer materials, such as aluminum, pure titanium or annealed stainless steel are not employed. The dimensions of the blade depend on, inter alia, the application for the apparatus, type of matter to be removed, the internal size of the head, material comprising the blade, etc. The blade is usually thick enough to be durable, yet thin enough to permit large ports to be present and, in particular, the blade may tend to be relatively thin and narrow. For example, the blade may have a cross-sectional dimension of between about 0.1 to 0.5 mm.

For a cutter assembly composed of blades, the shape of the cutter assembly may be defined by the outer profile and arrangement of the blades. In one embodiment of cutter assembly, the proximal end 620 is larger than the distal tip 616. For example, the proximal end may have a diameter that is at least twice the diameter of the distal tip, as shown in FIG. 14. The cutter assembly may also be pear-shaped, wherein the cutter assembly has its largest diameter at a portion of the cutter assembly that is close to the proximal end and, from there, tapers to the distal tip.

Figure 15A:
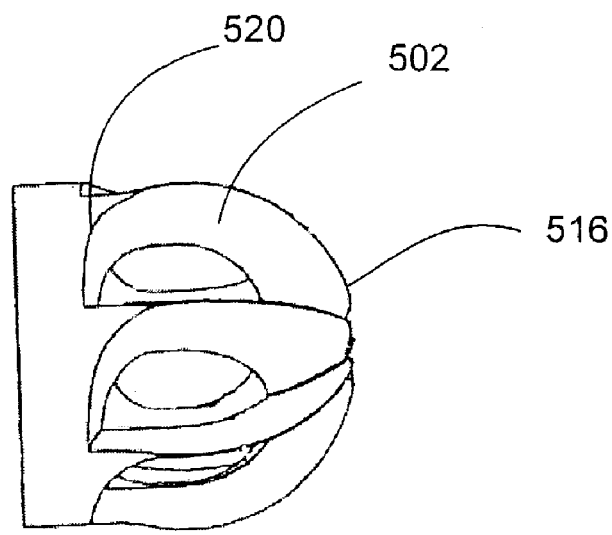
Figure 15B:
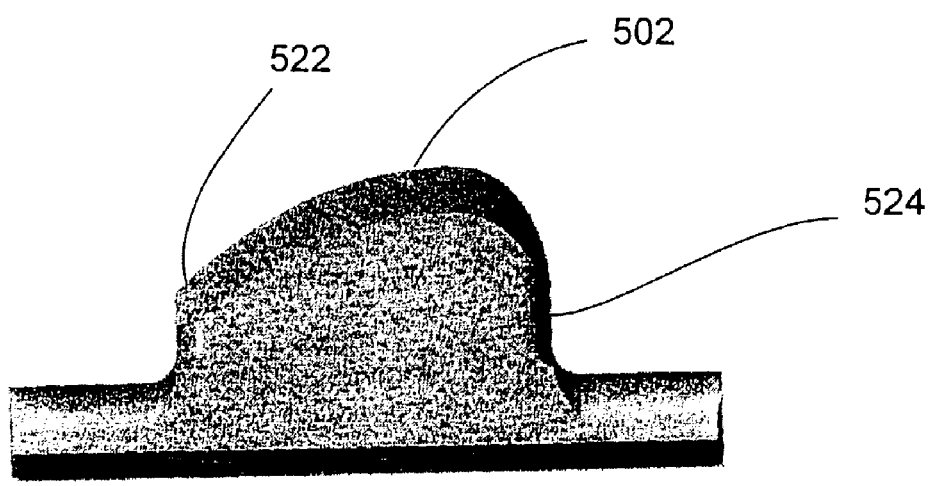

Another embodiment of cutter assembly 600 is depicted in FIG. 7A, wherein rather than pear-shaped, the cutter assembly is bullet-shaped and gradually widens from a narrow distal tip 616 to its proximal end 620. FIG. 15A shows a cup-shaped cutter assembly with multiple gradual sloping blades 602 from the distal tip 616 to the proximal end 620. Depicted in FIG. 15B is a single blade 602 having a gradual sloping blade profile, where the blade profile gradually slopes from one end, such as the blade's distal tip 622, to the other end, such as the blade's proximal end 624. This gradual sloping profile of the blade is without abrupt points that may cut into wanted matter within the body as the cutter assembly is guided toward the removal site.

In addition, in one embodiment the contour of the inner surface of a blade may at least substantially match the contour of the outer surface of the blade. For example, the inner surface may have at least considerably the same curvature as the curved profile of the outer surface. The relatively constant chord from proximal to distal ends of the blade may provide strong and thin qualities, advantageous for the present head design. Moreover, this embodiment permits large port gaps to be created between the blades. In addition, in some embodiments the blades may also have a straight and non-sweeping shape. However, in other embodiments, the blade may have any of a variety of shapes, including sweeping, suitable for its particular application.

Although particular shapes of blades are described herein, the blades may also be of a variety of shapes and sizes have a leading face. For example, the blade may have an asymmetrical or a symmetrical curved profile. Furthermore, the blades may be arranged and positioned in the cutter in a variety of ways.

Figure 16A:
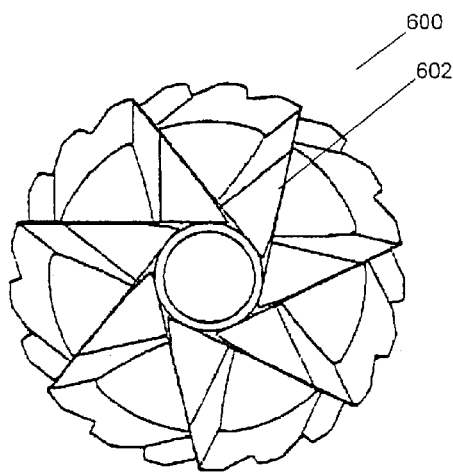
Figure 16B:
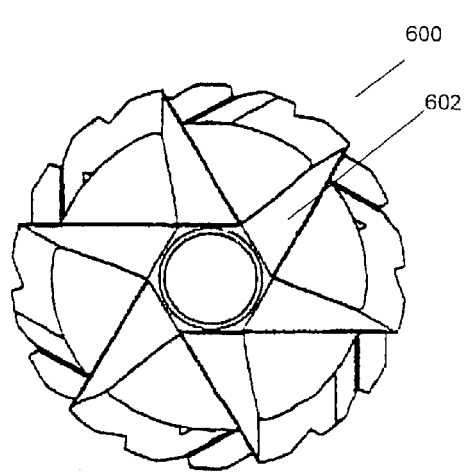
Figure 16C:
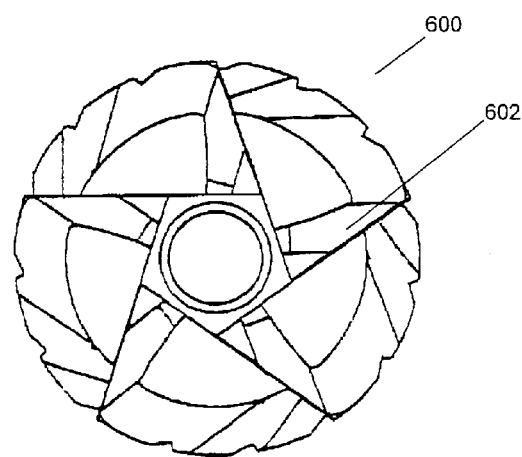
Figure 16D:
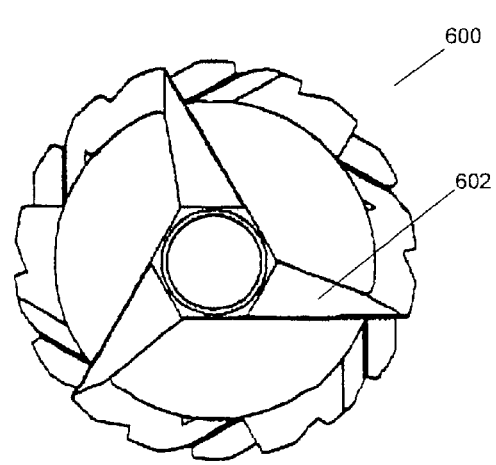

There may be any number of blades 602 provided in a cutter assembly 600, as shown variously in the examples in FIGS. 16A to 16D. FIG. 16A depicts a seven blade head, whereas FIG. 16B depicts a six blade head, FIG. 16C shows a five blade head and FIG. 16D illustrates a three blade head. Generally, according to this embodiment, the greater the number of blades, the close together the blades must be placed and consequently the smaller the port size.

As illustrated in the exemplary embodiments, the size and shape of the ports 614 may be defined, at least in part, by the size and shape of the blades and the spacing of the blades relative to each other. Typically, the ports comprise a large portion of the cutter assembly to permit greater aspiration of matter. A high port to blade ratio may be provided with the present embodiment without compromising differential cutting ability. In one embodiment, the total port area, i.e. surface area of the cutter assembly dedicated to ports, to total blade area, i.e. surface area of the cutter assembly dedicated to blades, is equal to or greater than about 1:1, such as about 3:1. For instance, a head that has five blades, each with a 1.75 mm O.D. tip and five ports, each port with an area of about 0.43 mm$^2$, results in a port to blade area ratio of about 3.32:1 according to the exemplary cutter assembly design. The ports according to the present invention described herein permit highly efficient aspiration of matter.

Figure 17A:
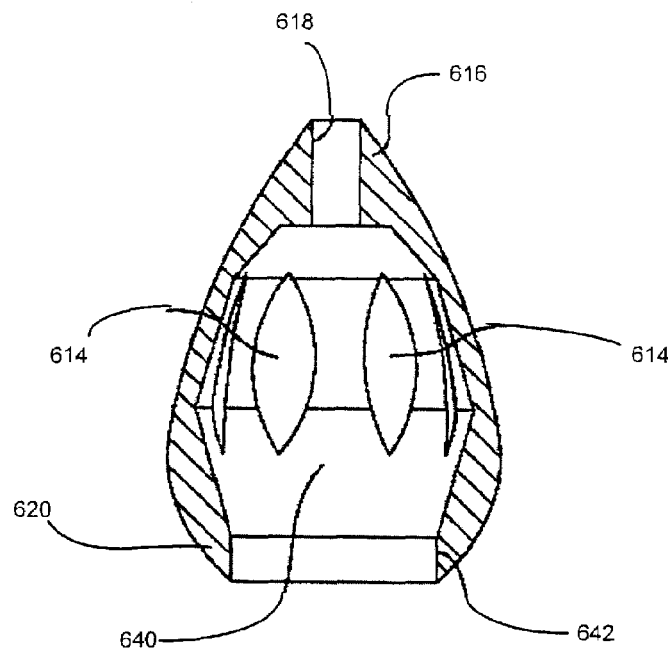

An internal view of a cutter assembly 600 is represented in FIG. 17A, wherein ports 614 may be provided as relatively large openings that may open to internal cavity 640. This expansive size of the ports permits efficient collection of materials and may not require a pumping action caused by sweeping blades to encourage materials into the port. Furthermore, the ports of this size need not be shaped to angle from a distal surface opening and to a proximal direction that leads to the interior of the cutter assembly, as is needed in some other devices to promote movement of materials into the ports. Since the present ports may be simple openings rather than angled channels, the manufacturing of the parts may also be simplified.

The ports usually provide communication between the removal site and the conduit of the removal system through the internal cavity 640. For example, the internal cavity 640 of the cutter assembly may be in communication with and terminate at the conduit, or other connecting component of the removal apparatus, to provide a collar 642 at the proximal cutter assembly end 620. The collar may have a diameter that generally corresponds to the outer diameter of a connecting component, such as a drive shaft, catheter, sheath, etc. to form a sealed pathway to and from the cutter head. At the distal end of the cutter assembly, there may be a distal tip 616 that may provide for translation of the cutter assembly over a guide wire. In some embodiments, the central bore 618 may extend from the distal tip 616 to the internal cavity 640. In some cutting assemblies, the internal cavity 640 may have a diameter greater than that of central bore 618.

Figure 17B:
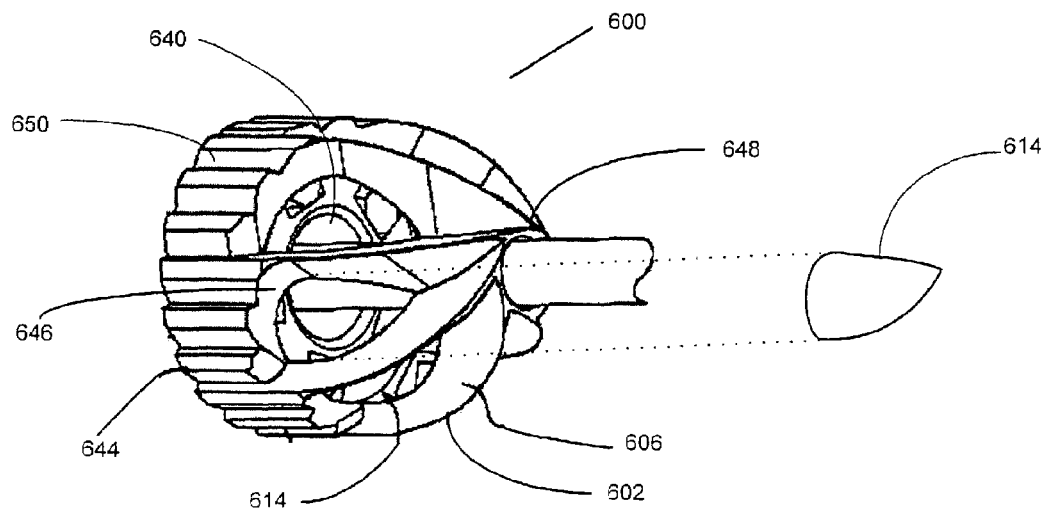

FIG. 17B depicts the shape of a port 614 exploded from cutter assembly 600 as created by the space, i.e. gaps, between adjacent blades 602. The profile of the port may be defined by the contour of the opposing blade's facing surface 606 and the amount of space between the blades. In embodiments that have blades closer to each other at one end of the blade, e.g. the distal end, than the other blade end, e.g. the proximal end, the ports may be advantageously at least substantially triangular in shape to enhance gathering of loose material. A tip of the triangular-shaped port may be pointing toward the cutter assembly's distal end and the facing surfaces of opposite blades may define two sides of the triangular port. The third side of the triangular port may be at the proximal end of the cutter assembly as defined by the proximal face 646 of a proximal ring 644 that contacts the proximal end of the blades.

The proximal ring 644 may be positioned in contact with the proximal end of the blades in order to secure the blades in a position relative to each other. A distal ring 648 may also be provided to secure the blades and may be positioned in contact with the distal end of the blades. Oftentimes, the entire proximal ring, or at least the proximal face portion, is larger than the distal ring at its contact point with the blades.

The proximal ring 644 may also include an outer ablation surface having a plurality of micro-flutes 650 to contact and cut the intracorporeal matter. The micro-flutes are usually small projections on the proximal ring and may have sharp cutting edges. The micro-flutes may be used for differential cutting at the outermost diameter of the head, where contact with beneficial soft tissue may occur. In this case, the flutes may be at angles of less than or equal to 90 degrees as described above with regard to blade angles. These small flutes may also break up friction that is frequently encountered where the proximal ring does not include such flutes and is generally smooth. Ports may or may not be included between the micro-flutes.

Figure 18A:
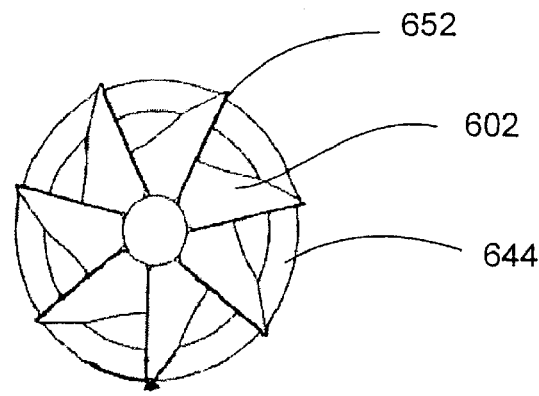
FIGS. 18A to 18C are schematic diagrams illustrating a cutter assembly embodiment wherein cutter blades protrude beyond the diameter of a proximal ring.
Figure 18B:
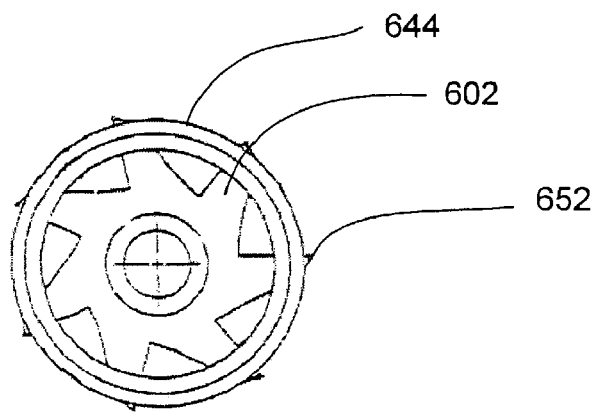
Figure 18C:
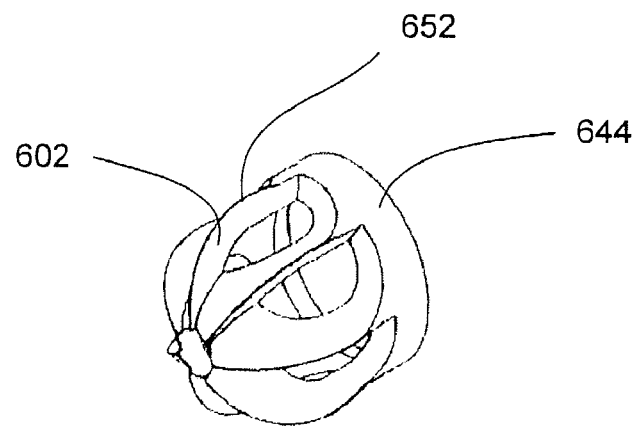

In one embodiment, as depicted, for example, in FIGS. 18A to 18C, the tips 652 of the blades 602 are extended farther than the outer diameter of the proximal ring 644 and/or greater than the diameter of a connecting conduit. The blades may protrude very slightly beyond the outer profile of the ring, such as between about 0.001 and 0.010 inch, and commonly about 0.001 and 0.005 inch. These protruding blades may prevent the proximal ring from interfering with the cutting action of the blades. Furthermore, where blade angles are acute, the tips do not typically cause harm to wanted tissue when the cutter assembly is not rotated at the removal site. Because the blades cause scraping rather than cutting. Furthermore, the gentle angle of the blade tips resist cutting into tissue as the cutter assembly is guided to the removal site without rotation.

In some embodiments of a removal system that have more than one cutter in a cutter assembly, e.g. a dual cutter assembly having a distal cutter and a proximal cutter as described above with regard to the adjustable and fixed cutters, either or all of the cutters in this multiple cutter assembly may be designed for differential cutting. The differential cutting design may be the same as or similar to the blade and port configurations described above with regards to FIGS. 14 to 18. The blade angles of the proximal cutter may be the same as, or different from the blade angle of the distal cutter. For example, the blade angle of the distal cutter and proximal cutter may be from about 45 to less than 90 degrees, and commonly the distal cutter may be about 55 to 75 degrees and the proximal cutter about 45 to 65 degrees. In another embodiment, the cutter assembly has a single cutter that is expandable and is designed for differential cutting, as described above in relation to the expandable cutter in a dual cutter assembly.

Figure 19A:
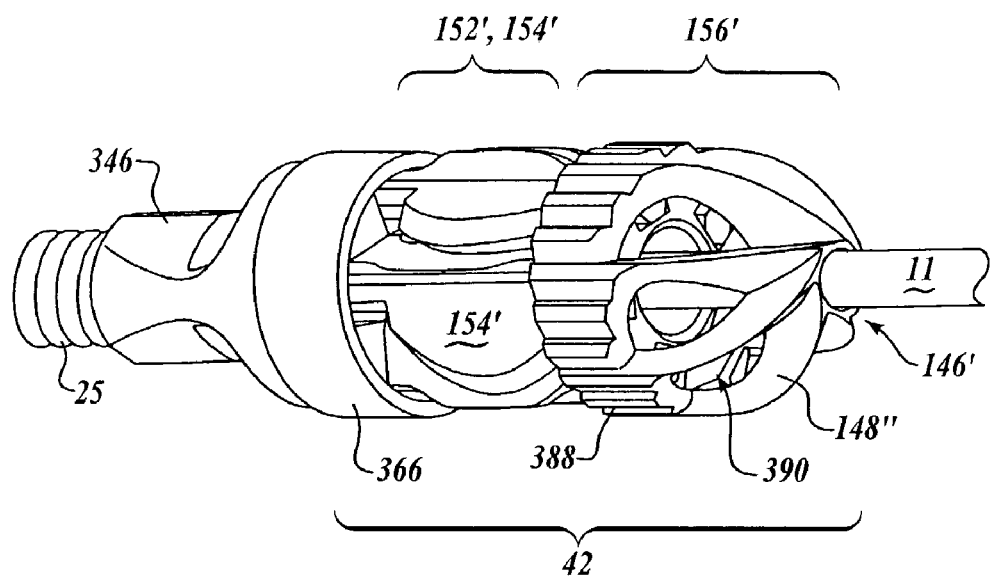
FIG. 19A shows an alternative embodiment of an expandable cutter assembly in the contracted configuration, and FIG. 19B provides a front perspective of the alternative embodiment of the present invention illustrated in FIG. 19A.
Figure 19B:
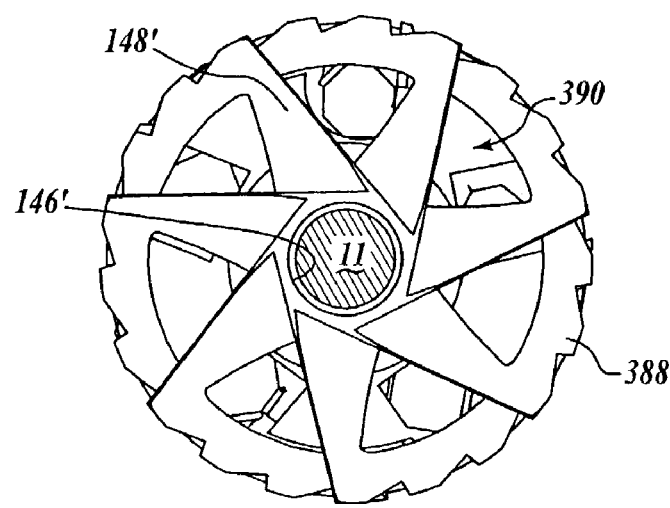

Similar to embodiments previously described, FIGS. 19A to 19B illustrate cutter assembly 42' in a contracted and expanded configuration, respectively. Cutting members 154' may freely rotate within recesses 380 of central block 154' and, depending on the direction of rotation, rotate from a tangential orientation, in which blade sections of cutting members engage respective support faces 140' (i.e., contracted configuration) to a radial orientation in which blade sections of cutting members 154' are in contact with stop faces 142' of central block 152' (i.e., expanded configuration). Stop faces 142' check rotational movement of blade members and provide support while operating in the expanded configuration.

Figure 20A:
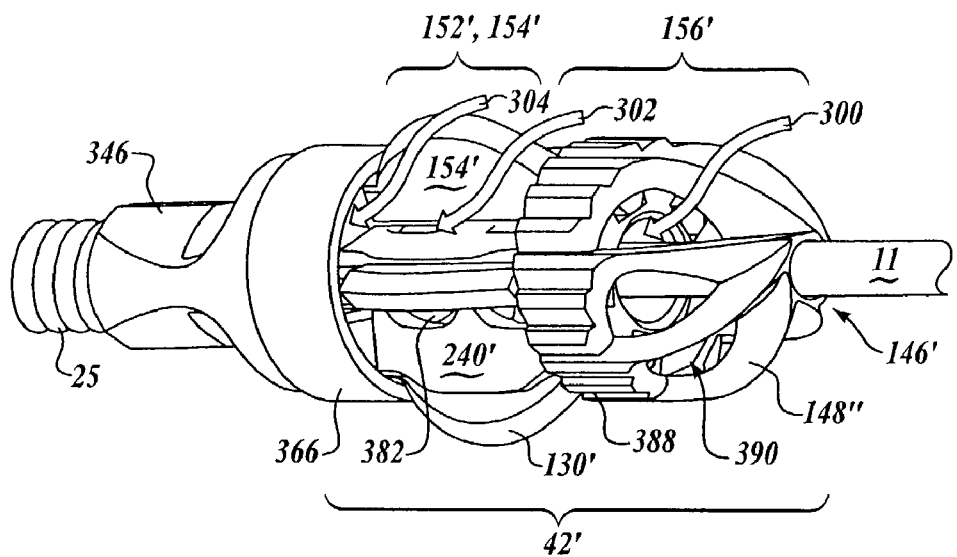
FIG. 20A shows an alternative embodiment of an expandable cutter assembly in the expanded configuration and FIG. 20B provides a front perspective of the alternative embodiment of the present invention illustrated in FIG. 20A.
Figure 20B:
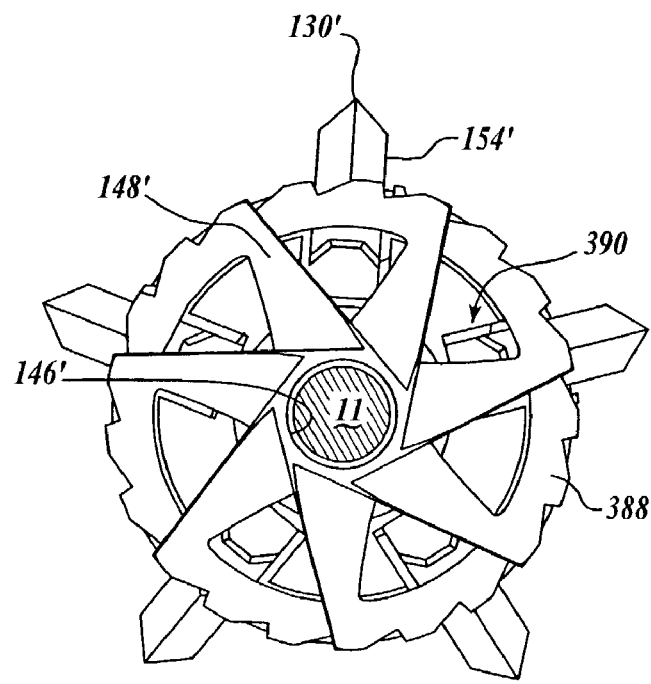

The same general principles of operation described above apply to the embodiment depicted in FIGS. 20A-20B. Notably, one embodiment provides a fixed diameter distal cutter 156' having cutting flutes 148' that immediately engage occlusive material. Additionally, the embodiment may provide a comparatively large aspiration conduit area by virtue of the large aspiration cutouts or ports 390. During aspiration, aspirate and particulates are may be drawn through aspiration cutouts, or ports 390 of distal cutter 156', ports 382 of central block 152', as well as spaces between central block 152' and proximal cap 366, as depicted by arrows 400, 402 and 404, respectively.

It will be understood that the foregoing discussion merely illustrative of the invention and its principles. However, modifications and variations in the details of the disclosure will occur to those skilled in the art to which this invention relates and still remain within the scope and principles of the invention. It will be understood that obvious variations and modifications thereof that may be made by those skilled in the art are intended to be included within the spirit and purview of this application and the scope of the appended claims.

We claim:

1. An assembly to remove matter from a cavity in a body, comprising:
   multiple blades capable of removing the matter using differential cutting techniques, each blade having a facing surface presented in front of an opposing blade facing surface and each blade positioned to form an acute blade angle of attack of between about 30 degrees and about 90 degrees;
   at least two ports to remove the matter, each port being positioned between the facing surfaces of two opposing blades;
   a conduit in communication with the ports to direct the removed matter away from the site of the matter; and
   a distal ring in contact with the blades at the distal end of the blades and a proximal ring having a proximal ring face in contact with the blades at the proximal end of the blades, the proximal ring being larger than the distal ring, and the ports being defined by the proximal ring face and the opposing blade's facing surfaces.

2. The assembly of claim 1, wherein the acute blade angle of attack is greater than or equal to about 45 degrees and less than 90 degrees.

3. The assembly of claim 1, wherein the acute blade angle of attack is less than or equal to about 75 degrees.

4. The assembly of claim 1, wherein the blades have a cross-sectional dimension of between about 0.1 to 0.5 mm.

5. The assembly of claim 1, wherein the proximal ring includes an ablation surface having a plurality of micro-flutes to cut the matter.

6. The assembly of claim 1, wherein the blades protrude beyond the outer diameter of the proximal ring.

7. The assembly of claim 1, further comprising at least one infusion port in proximity to the cutting assembly for infusing a liquid.

8. A method of removing matter from a cavity in a body, comprising:
   rotating a cutter assembly having circumferential positioned multiple blades and at least two ports, each port being located between facing surfaces of opposing blades, each of the blades having a leading face;
   as the cutter assembly rotates, sequentially contacting each of the blades with a surface of the matter at a blade contact point, wherein the leading face of the blade forms an acute blade angle of attack;
   moving the cutter assembly in the direction of the acute blade angle to scrape the matter; and
   aspirating the scraped matter through the ports,
   wherein moving the cutter assembly along the matter includes moving the cutter assembly along a support surface that contacts the matter and the support surface deforms away from the blade contact point.

9. The method of claim 8, further comprising infusing a liquid in proximity to the cutter assembly.

10. A system for removing matter from a cavity in a body, comprising:
    a drive shaft that is rotatable;

a drive system operably coupled to the drive shaft for rotating the drive shaft; and a cutter assembly coupled to the drive shaft, the cutter assembly comprising a proximal cutter and a distal cutter, wherein at least one of the proximal and distal cutters comprises multiple blades having leading edges positioned to form an acute blade angle of attack with the matter, and wherein the distal cutter has a fixed diameter and the proximal cutter has an adjustable diameter.

11. The system of claim 10, wherein each blade has a facing surface presented in front of an opposing blade facing surface, and the system further comprises at least two aspiration ports to remove the matter, each port being positioned between the facing surfaces of two opposing blades.

12. The system of claim 10, further comprising at least one infusion port in proximity to the cutting assembly for infusing a liquid.

* * * * *